(12) United States Patent
Parazynski et al.

(10) Patent No.: US 11,945,021 B2
(45) Date of Patent: Apr. 2, 2024

(54) SYSTEMS AND METHODS FOR BENDING A NEEDLE

(71) Applicant: BendRx, Inc., Houston, TX (US)

(72) Inventors: Scott Edward Parazynski, Houston, TX (US); John Spiegel Michels, Jr., Dallas, TX (US); Jeffrey William Bull, Naperville, IL (US); Roy Melling, Borrego Springs, CA (US)

(73) Assignee: BendRx, Inc., Houston, TX (US)

( * ) Notice: Subject to any disclaimer, the term of this patent is extended or adjusted under 35 U.S.C. 154(b) by 0 days.

(21) Appl. No.: 18/148,806

(22) Filed: Dec. 30, 2022

(65) Prior Publication Data

US 2023/0381846 A1  Nov. 30, 2023

Related U.S. Application Data

(60) Provisional application No. 63/345,255, filed on May 24, 2022.

(51) Int. Cl.
*B21D 7/04* (2006.01)
*A61B 17/34* (2006.01)
*A61B 17/00* (2006.01)

(52) U.S. Cl.
CPC ............ *B21D 7/04* (2013.01); *A61B 17/3401* (2013.01); *A61B 2017/00526* (2013.01)

(58) Field of Classification Search
CPC .................................. B21D 7/04; B21F 1/002
See application file for complete search history.

(56) References Cited

U.S. PATENT DOCUMENTS

| 5,201,210 A | 4/1993 | Stein, III |
| 11,014,141 B1 | 5/2021 | Parazynski et al. |
| 2003/0045839 A1 | 3/2003 | Yoshio et al. |
| 2011/0224626 A1 | 9/2011 | Lin et al. |

FOREIGN PATENT DOCUMENTS

WO  WO-2022060778 A1  3/2022

OTHER PUBLICATIONS

International Search Report and Written Opinion for International Application No. PCT/US2022/082644 dated Apr. 10, 2023, 11 pages.
Non-Final Office Action, dated Feb. 3, 2021, for U.S. Appl. No. 17/037,568 (7 total pages).

*Primary Examiner* — Teresa M Ekiert
(74) *Attorney, Agent, or Firm* — COOLEY LLP

(57) ABSTRACT

A needle bending assembly configured to at least temporarily contain a needle can include a first housing section, a second housing section, and a coupling element coupled between the first housing section and the second housing section. The first housing section defines a first cavity configured to at least temporarily contain a first section of the needle. The second housing section defines a second cavity configured to at least temporarily contain a second section of the needle forming a distal tip. The coupling element is configured such that when the needle is contained within the housing sections, movement of the second housing section relative to the first housing section results in a bending of the needle at a location corresponding to the coupling element.

19 Claims, 21 Drawing Sheets

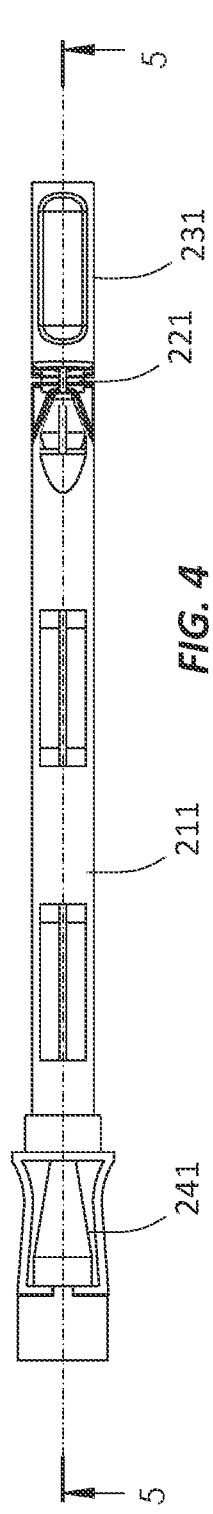
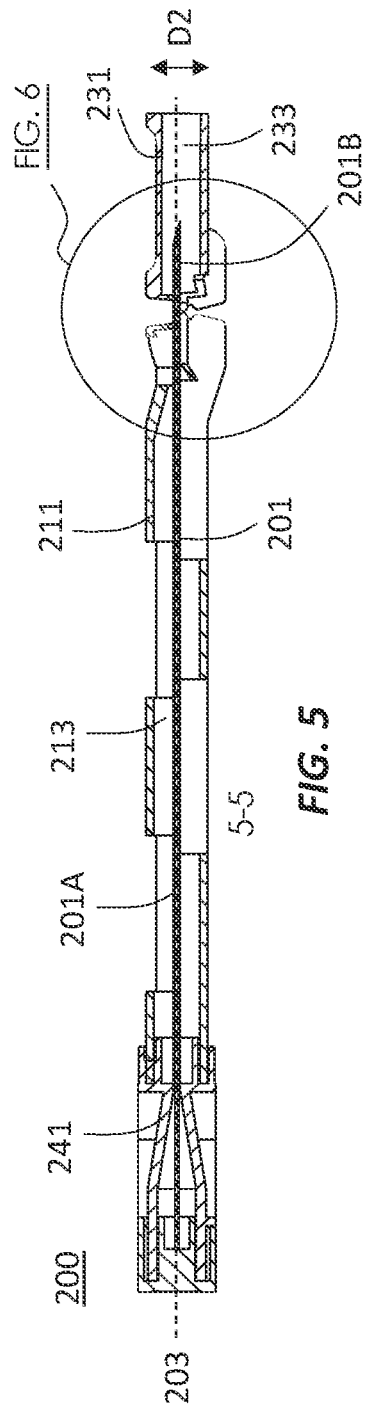
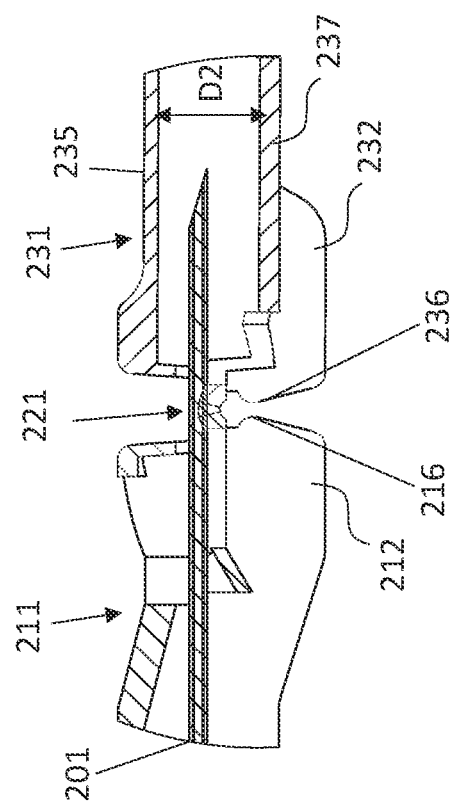

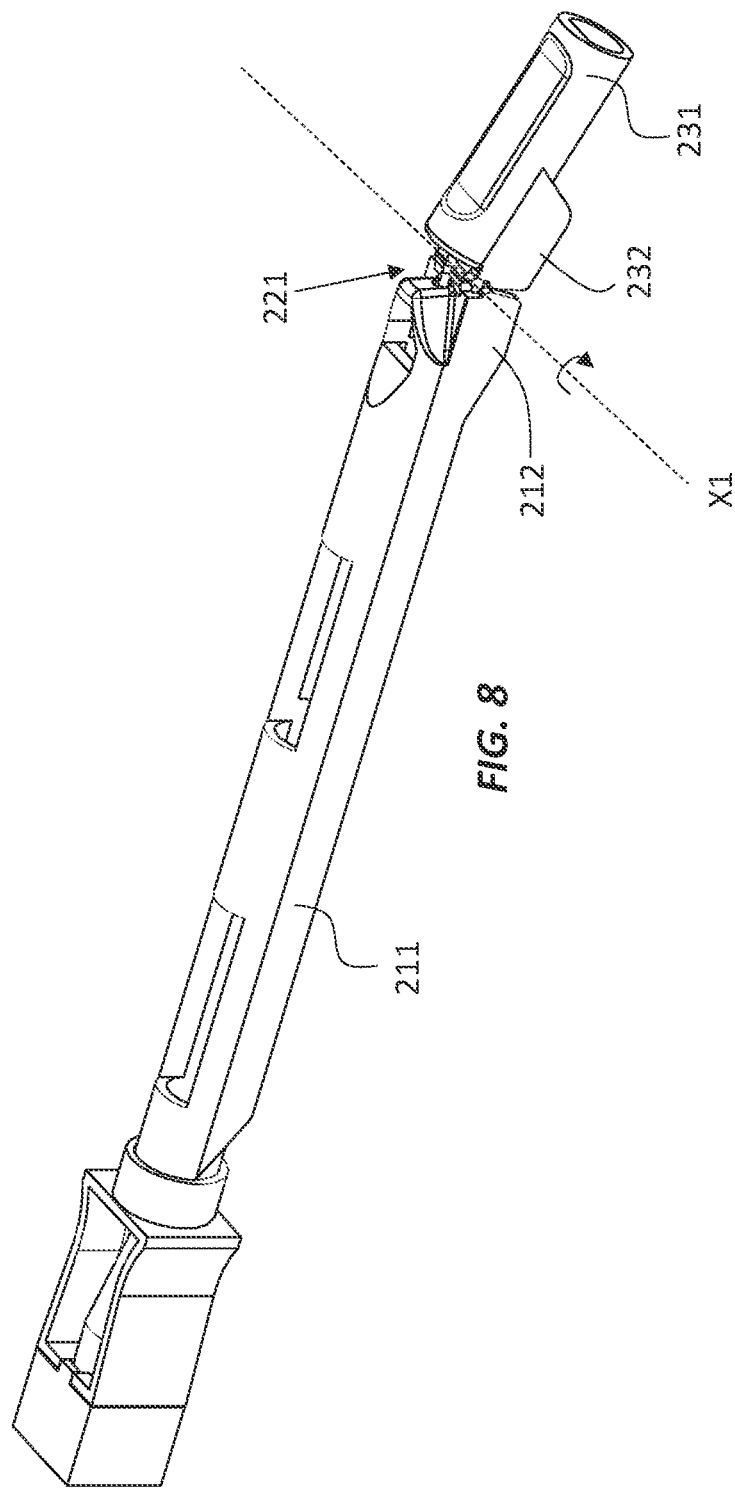

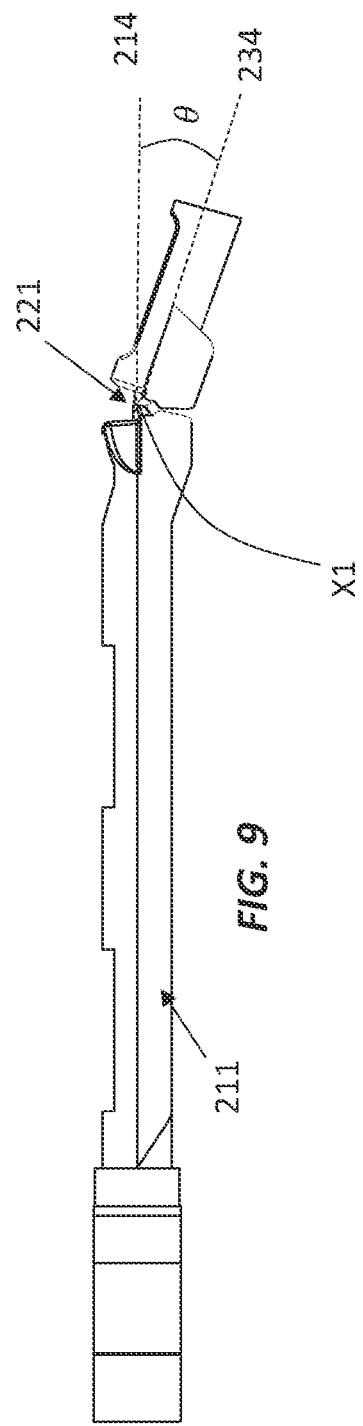

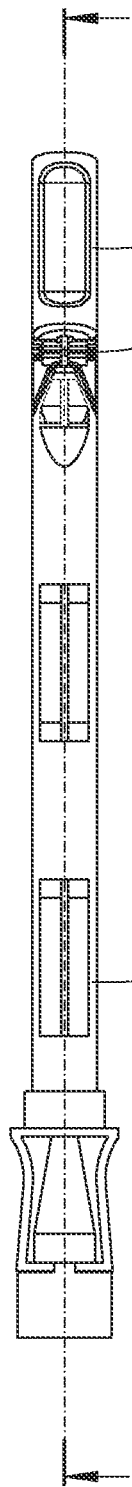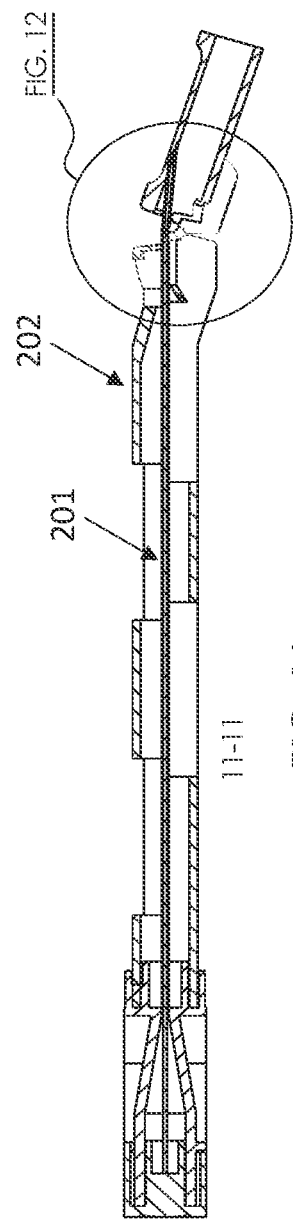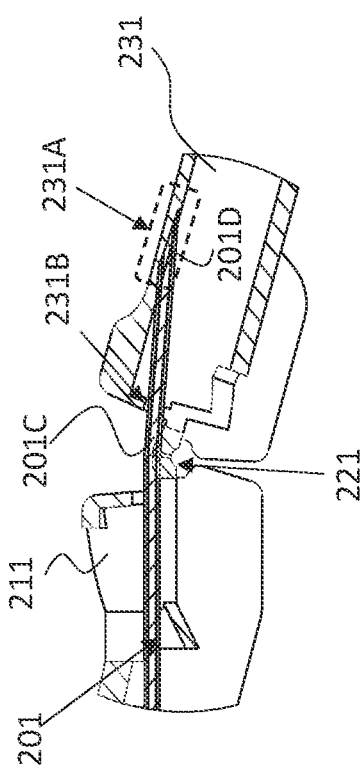
FIG. 10
FIG. 11
FIG. 12
FIG. 13

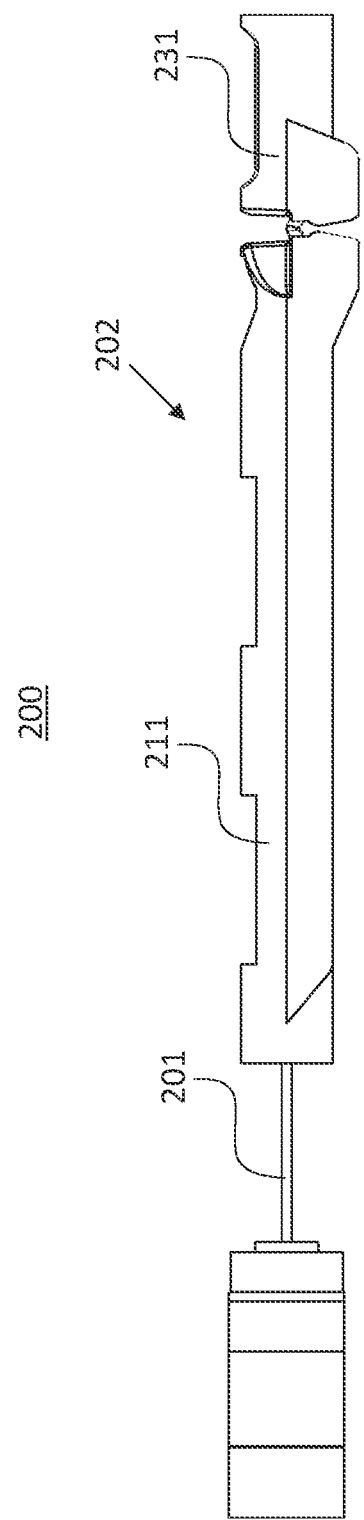

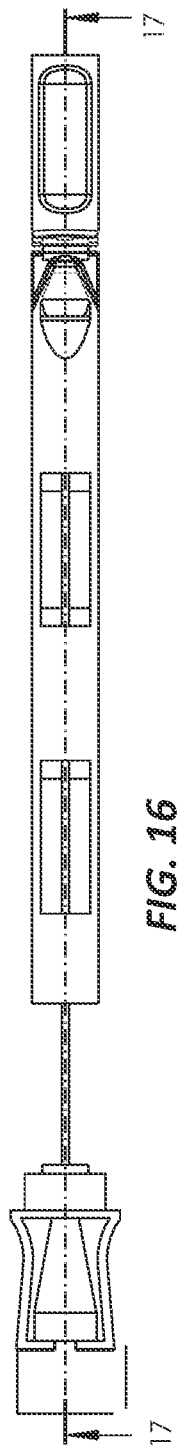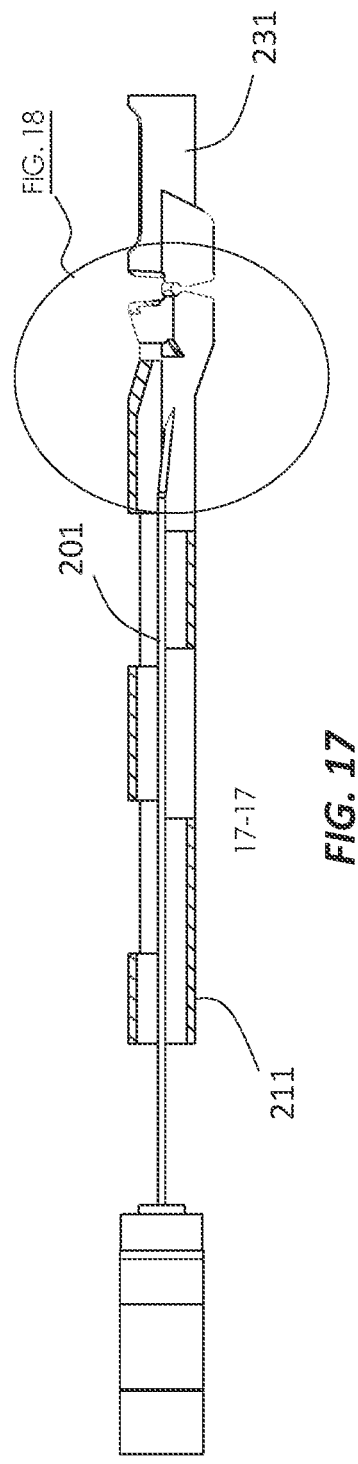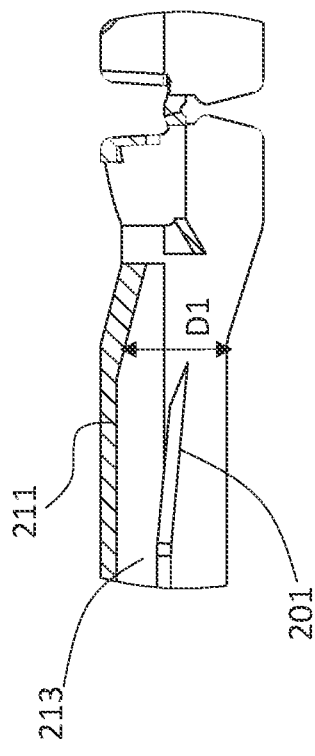

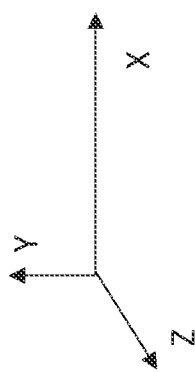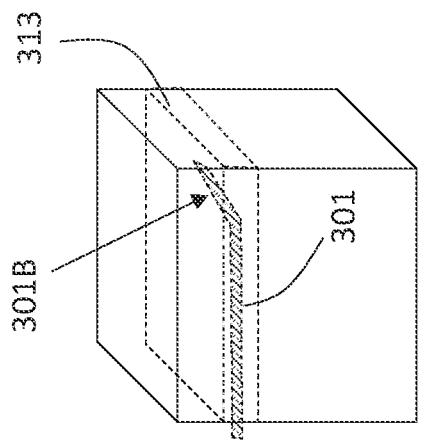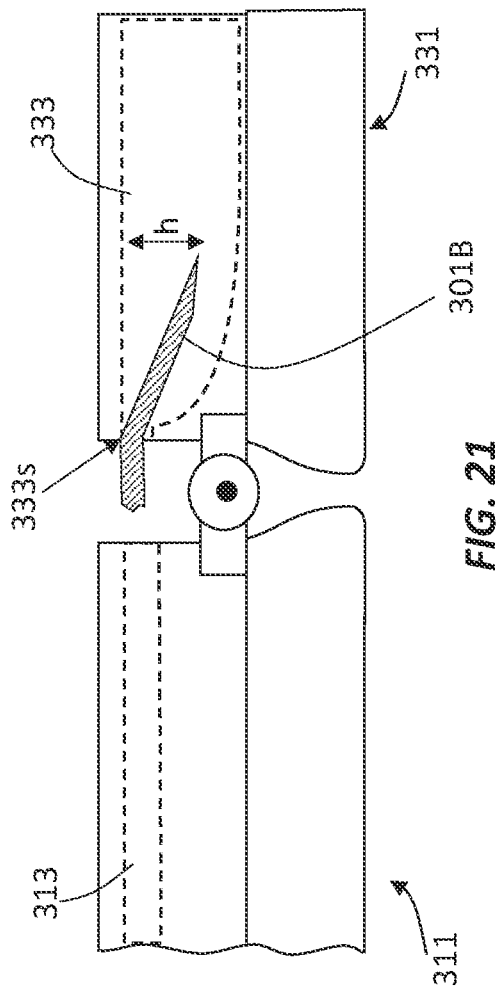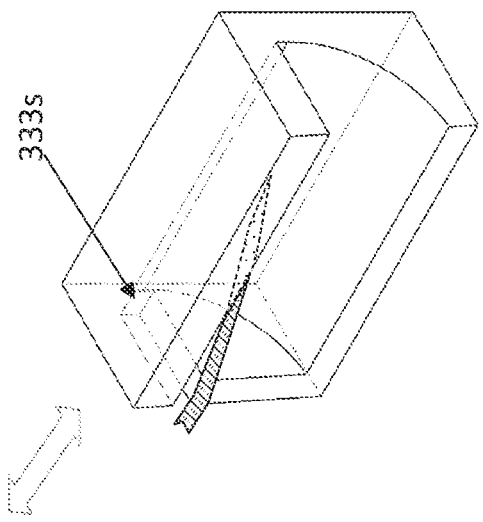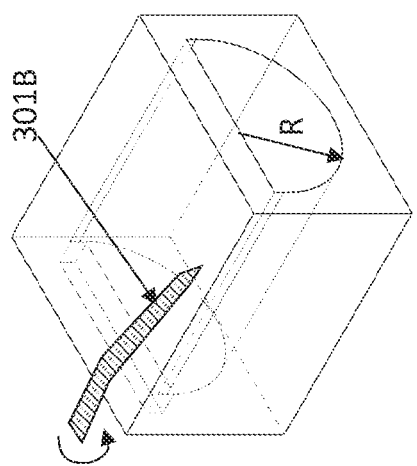
FIG. 21
FIG. 22
FIG. 23
FIG. 24

SYSTEMS AND METHODS FOR BENDING A NEEDLE

CROSS-REFERENCE TO RELATED APPLICATIONS

This application claims priority to and the benefit of U.S. Provisional Patent Application No. 63/345,255, filed May 24, 2022, entitled "Systems and Methods for Bending a Needle," the disclosure of which is incorporated herein by reference in its entirety.

TECHNICAL FIELD

The present disclosure generally relates to systems and methods for bending needles. More specifically, the present disclosure relates to systems and methods for bending needles such as spinal needles and biopsy needles, which in some instances, may contain an indwelling stylet.

BACKGROUND

Certain therapeutic and diagnostic medical procedures involve the use of long spinal needles that are bent by the physician just prior to an interventional procedure near their tip to facilitate steering towards an intended target. These procedures, typically done using radiologic guidance (e.g., intermittent fluoroscopy), often include maneuvering around skeletal and other vital structures to get to their intended target. In typical practice, a physician would use a needle driver, a type of a surgical instrument intended to grip a surgical needle, to pinch the end of a spinal needle and then introduce a subtle bend in the tip (e.g., approximately 5 degrees in magnitude).

Alternatively, physicians will sometimes also bend needles using just their gloved hands, risking loss of sterilization of the needle due to inadvertent puncture of their glove as well as risk a needlestick injury. Another unsatisfactory method of bending procedural needle tips involves the use of a needle sheath or cap, applied loosely to a distal needle tip to bend it with coarse control.

Challenges with some known techniques of manually bending a needle tip can include, for example: a) the inexact and/or non-reproducible nature of the bend; b) the "off-axis" nature of the bend, as bending may unintentionally take place in two axes given the way the needle driver grasps the needle tip; c) risk of unintentional needlestick injury to the physician while manipulating the needle during the bending process; d) risk of damage to the needle itself such as the cutting surfaces of the needle bevel or tip or the pinching of the inner lumen of the needle; e) the cost of additional surgical tools, cleaning and sterilization cycles for every procedure; f) the lost time for the physician and support staff, and/or the like. Furthermore, the forces associated with bending a needle containing a stylet may exceed those achievable by using finger pressure alone.

In effort to mitigate these or other challenges, some known needles can be pre-bent and/or otherwise manufactured to include a bend. Such known needles, however, are substantially more expensive and do not give the option for performing a procedure with a straight needle tip.

Some known needle bending systems attempt to solve the challenges described above such as, for example, those described in U.S. Pat. No. 11,014,141, filed Sep. 29, 2022, entitled, "Needle Bending Assembly," the disclosure of which is incorporated herein by reference in its entirety. Nonetheless, there exists a need for a device, system, and/or a method for bending needles, such as spinal needles, biopsy needles, and/or the like. Furthermore, there exists a need for incorporating such devices and/or systems into a sterile packaging of a needle.

SUMMARY

The present disclosure presents system and methods for bending needles such as spinal and/or biopsy needles. Consistent with a disclosed embodiment, a needle bending assembly configured to at least temporarily contain a needle can include a first housing section, a second housing section, and a coupling element coupled between the first housing section and the second housing section. The first housing section defines a first cavity configured to at least temporarily contain a first section of the needle. The second housing section defines a second cavity configured to at least temporarily contain a second section of the needle forming a distal tip. The coupling element is configured such that when the needle is contained within the housing, movement of the second housing section relative to the first housing section results in a bending of the needle at a location corresponding to the coupling element.

BRIEF DESCRIPTION OF THE DRAWINGS

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

FIGS. 2-6 are various views of a needle bending system in a first configuration in which a needle is disposed in needle bending assembly in an unbent state, according to an embodiment.

FIGS. 7-12 are various views of the needle bending system of FIG. 2 in a second configuration in which the needle bending assembly has been manipulated to bend the needle disposed therein.

FIGS. 13-18 are various views of the needle bending system of FIG. 2 in a third configuration and showing the bent needle being withdrawn from the needle bending assembly.

FIGS. 20-24 are various views of one or more portions of the needle bending system of FIG. 19 shown in a second configuration.

DETAILED DESCRIPTION

Figure 1A:
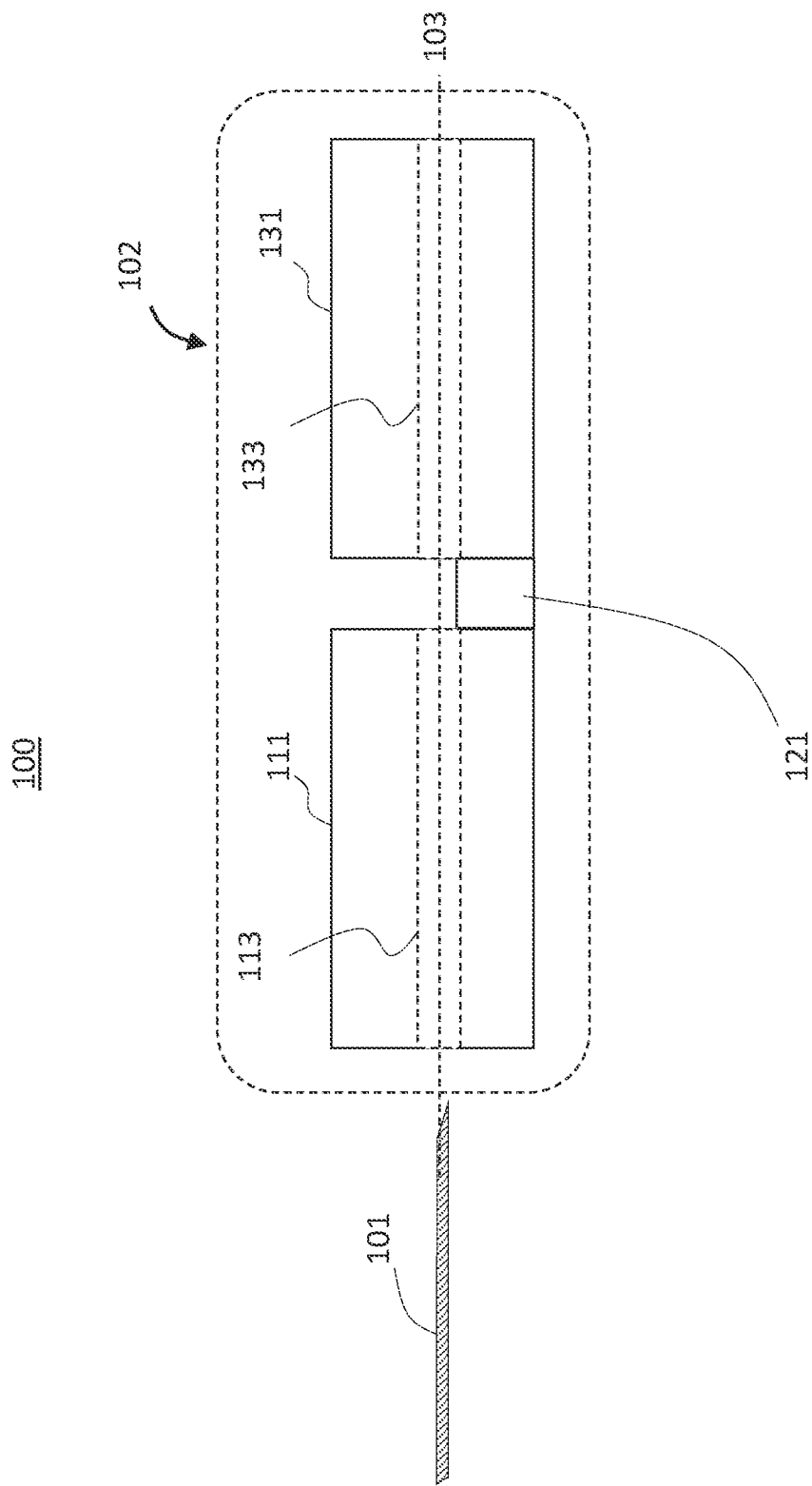
FIG. 1A is a schematic illustration of a needle bending system for bending a needle, according to an embodiment.

Aspects of the present disclosure are related to system and methods for bending needles, such as spinal and/or biopsy needles, with or without indwelling stylets. The following detailed description is not to be taken in a limiting sense but is made merely for the purpose of illustrating the general principles of the invention. In some cases, the system for bending a needle (needle bending system) may include a needle bending assembly and a needle. In some cases, the needle bending system may be prepackaged and sterilized, and contain a straight needle placed in an enclosure or housing of the needle bending assembly for bending. In such cases, an end user such as a physician, doctor, surgeon, nurse practitioner, nurse anesthetist, operating room technician, scrub nurse, etc., may manipulate the needle bending system to impart a desired bend in the needle, as described in detail herein respect to specific embodiments.

The embodiments described herein can be used to bend any suitable type or size of needle. While specific examples may be described, it should be understood that such examples are not intended to be limiting in any way. In some implementations, for example, the embodiments described herein can be used to bend spinal needles. Generally, these needles are configured to be inserted into the spine (as well as other body tissues) at a predetermined angle to facilitate steering a tip of the needle to a desired target, typically aided by intermittent fluoroscopic guidance. In some implementations, such spinal needles can include an indwelling stylet or wire that fills or substantially fills the internal diameter of the spinal needle during insertion in the body, preventing tissue or fluid from traveling through the lumen of the needle. Once the tip of the needle is at a desired position, the stylet can be removed and fluid(s) can be injected into the body and/or removed from the body. Any of the embodiments described herein can be used, prior to insertion, to bend such needles to a desired and/or predetermined angle with or without the stylet disposed in the lumen. In other implementations, however, any of the embodiments described herein can be used to bend any suitable type or size of needle used for any suitable procedure and/or purpose. For example, in some implementations, any of the embodiments described herein may be used to bend a needle intended to be used in a procedure performed on a human patient, while in other implementations, any of the embodiments may be used to bend a needle intended to be used in a procedure performed on an animal or non-human patient. Moreover, in some implementations, the embodiments described herein can be used to bend devices and/or components other than needles.

In some embodiments, a needle bending assembly can include a housing configured to at least temporarily contain a needle. The housing has a first housing section, a second housing section, and a coupling element. The first housing section defines a first cavity configured to at least temporarily contain a first section of the needle. The second housing section defines a second cavity configured to at least temporarily contain a second section of the needle forming a distal tip. The coupling element is configured to couple the first housing section and the second housing section such that when the needle is contained within the housing, movement of the second housing section relative to the first housing section results in a bending of the needle at a location corresponding to the coupling element.

In some embodiments, a needle bending assembly configured to at least temporarily contain a needle can include a first housing section, a second housing section, and a coupling element coupled between the first housing section and the second housing section. The first housing section defines a first cavity configured to at least temporarily contain a first section of the needle. The second housing section defines a second cavity configured to at least temporarily contain a second section of the needle forming a distal tip. The coupling element is configured such that when the needle is contained within the housing, movement of the second housing section relative to the first housing section results in a bending of the needle at a location corresponding to the coupling element.

In some embodiments, a needle bending system includes a needle assembly and a needle bending assembly. The needle assembly has a needle extending in a distal direction from a needle hub. The needle bending assembly is removably coupled to the needle assembly. The needle bending assembly includes a first housing section defining a first cavity that removably contains a first section of the needle, a second housing section defining a second cavity that removably contains a second section of the needle forming a distal tip thereof, and a coupling element configured to couple the first housing section and the second housing section. The needle bending assembly configured such that movement of the second housing section relative to the first housing section results in a bending of the needle at a location corresponding to the coupling element.

In some embodiments, a needle bending assembly includes a first housing section, a second housing section, and a coupling element that couples the first housing section to the second housing section. In some implementations, a method of bending a needle using the needle bending assembly includes transitioning the second housing section relative to the first housing section from a first configuration into a second configuration. A section of the needle between the housing sections is engaged by the coupling element as a result of the transitioning and the needle is bent as a result of the coupling element engaging the section of the needle. The second housing section is allowed to transition from the second configuration toward the first configuration after the bending. The method then includes withdrawing the bent needle from each of the first housing section and the second housing section.

As used in this specification and appended claims, the singular form of the articles "a," "an," and "the," unless clearly indicated to the contrary, should be understood to mean "at least one."

As used in this specification and appended claims, the term "and/or" should be understood to include any and all combinations of one or more of the elements so conjoined (e.g., elements that are conjunctively present in some cases and disjunctively present in other cases). Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in this specification and appended claims, "or" should be understood to have the same meaning as "and/or" as defined above. For example, when separating items in a list, "or" or "and/or" shall be interpreted as being inclusive (e.g., the inclusion of at least one, but also including more than one of a number or list of elements, and, optionally, additional unlisted items). Only terms clearly indicated to the contrary, such as "only one of" "exactly one of" etc., will refer to the inclusion of exactly one element of a number or list of elements. In general, the term "or" as used herein shall only be interpreted as indicating exclusive alternatives (e.g., "one or the other but not both") when used in conjunction with terms of exclusivity, such as "either," "one of," "only one of," "exactly one of" etc.

As used in this specification and appended claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used in this specification and appended claims, the terms "about," "approximately," and/or "substantially" when used in connection with stated value(s) and/or geometric structure(s) or relationship(s) is intended to convey that the value or characteristic so defined is nominally the value stated or characteristic described. In some instances, the terms "about," "approximately," and/or "substantially" can mean and/or contemplate, generally, a value or characteristic stated within a desirable tolerance. For example, such a tolerance can be plus or minus 10% of the stated value (e.g., about 0.01 can include 0.009 to 0.011, about 0.5 can include 0.45 to 0.55, and about can include 9 to 11. Similarly, two or more objects may be described as having a size that is substantially equal when the sizes of the objects are nominally equal or within a tolerance of being equal. While a value, structure, and/or relationship stated may be desirable, it should be understood that some variance may occur as a result of, for example, manufacturing tolerances or other practical considerations (e.g., applied pressures, forces, temperatures, etc.). Accordingly, the terms "about," "approximately," and/or "substantially" can be used herein to account for such tolerances and/or considerations.

Figure 1B:
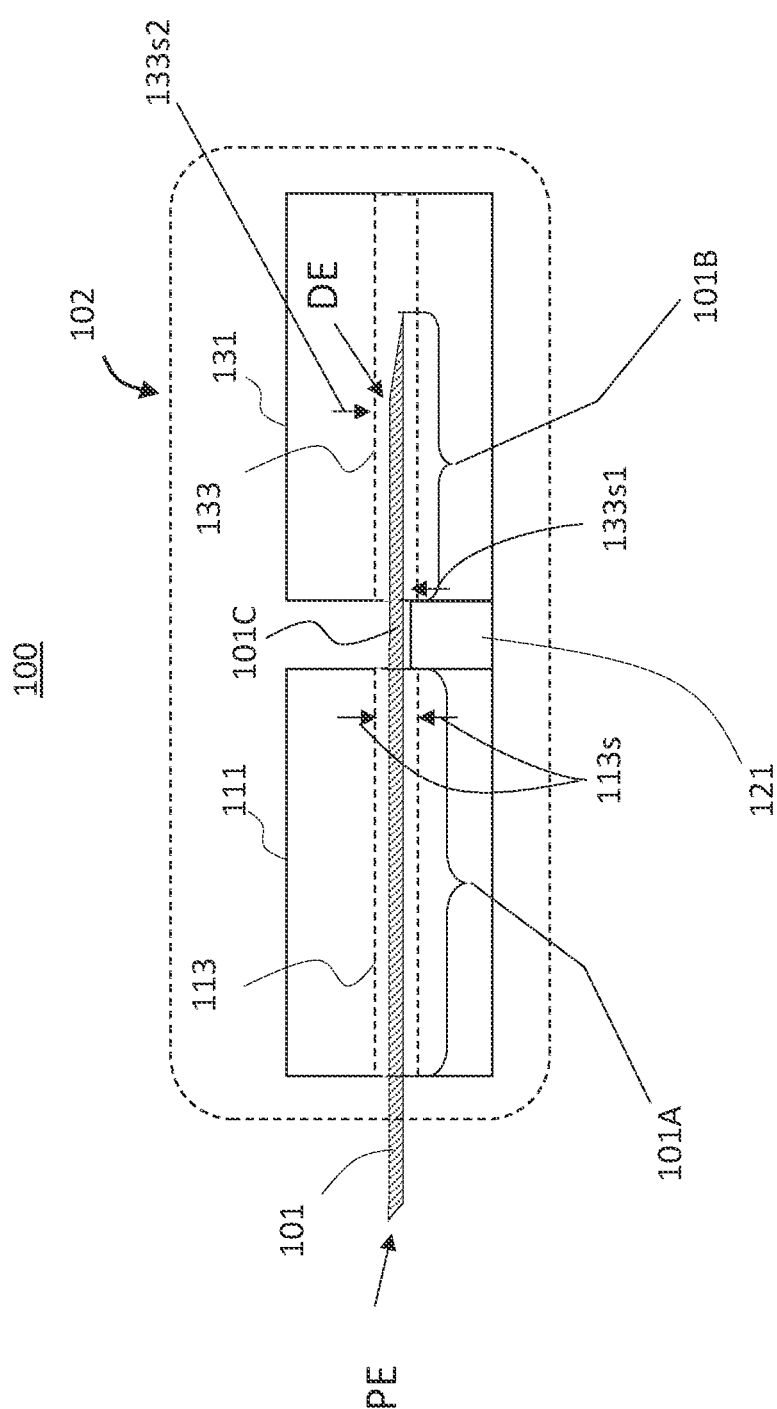
FIG. 1B is a schematic illustration of the needle bending system of FIG. 1A, shown with the needle placed within the needle bending assembly.
Figure 1C:
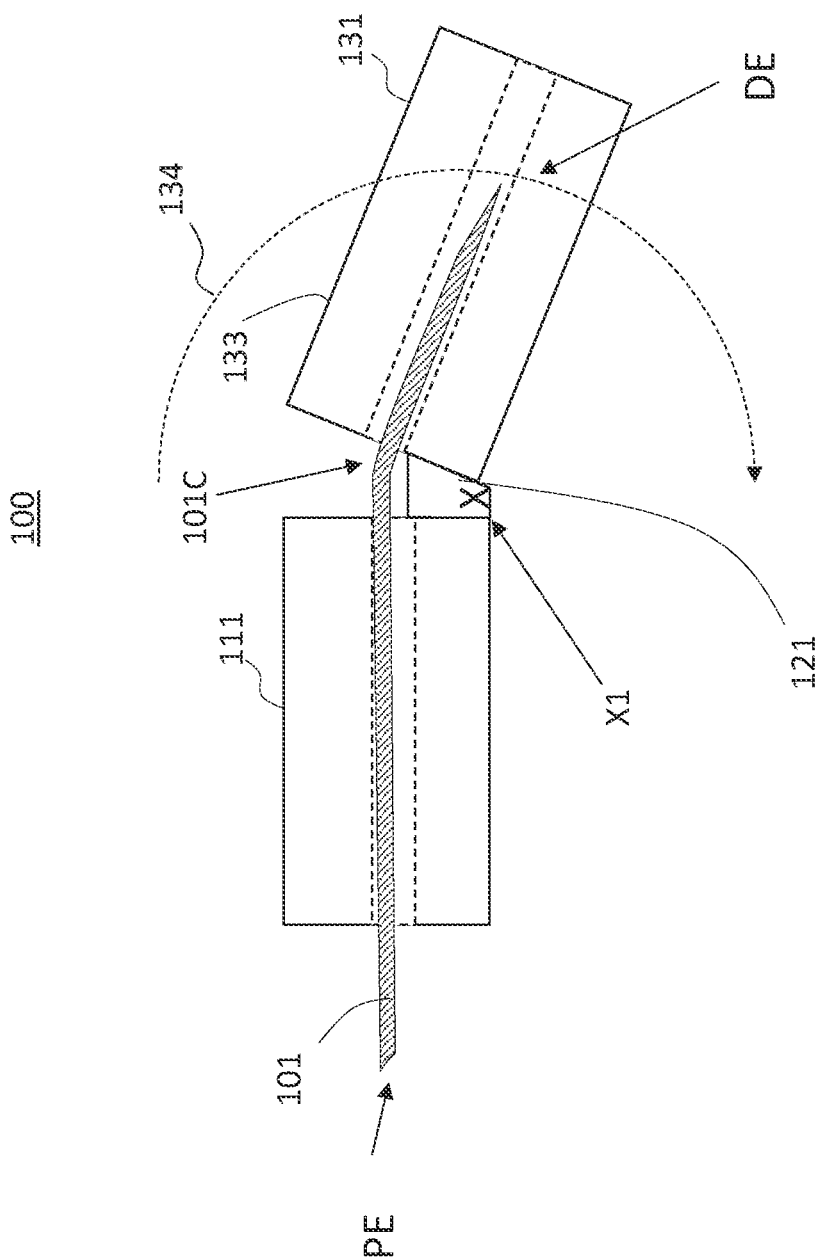
FIG. 1C is a schematic illustration of the needle bending system of FIGS. 1A and 1B, shown as having a first housing section and a second housing section, with the second housing section rotated relative to the first housing section.

Referring now to the drawings, an example embodiment of a needle bending system 100 is shown in FIGS. 1A-1C. The needle bending system 100 includes a needle bending assembly 102 and a needle 101 (which may be placed within the needle bending assembly 102, as shown in FIG. 1B). The needle bending assembly 102 includes a first housing section 111 and a second housing section 131 coupled to the first housing section 111 via a coupling element 121. In some embodiments, the needle bending assembly 102 can be a single-piece (e.g., monolithic), disposable device that can be manipulated to bend a needle disposed within the needle bending assembly 102, as described in further detail herein. In such embodiments, the coupling element 121 can be, form, and/or include a living hinge, and/or the like.

FIGS. 1A and 1B, show schematic cross-sectional side views of the needle bending system 100. The first housing section 111 and/or second housing section 131 (collectively referred to herein as "housing sections 111, 131") may have any suitable three-dimensional shape. For instance, the housing sections 111 and/or 131 may be substantially cylindrical, elliptical, polygonal, etc. in cross-section with the respective first cavity 113 and/or the second cavity 133 (collectively referred to herein as "cavities 113, 133") extending therethrough in a direction along a longitudinal axis 103 of the needle bending assembly 102, as shown in FIG. 1A. The housing sections 111 and 131 can have substantially the same cross-sectional shape or can have different or varying cross-sectional shapes. Similarly, the inner walls of each of the housing sections 111 and 131 can define the cavities 113 and 133, respectively, such that the cavities 113 and 133 have any suitable cross-sectional shape. The cavities 113 and 133 can have substantially the same cross-sectional shape or can have different cross-sectional shapes, which may be uniform or non-uniform along the length of each housing section 111 and 131 (e.g., in the direction of the longitudinal axis 103 shown in FIG. 1A).

The needle bending assembly 102 may be fabricated from any suitable material that has a sufficient or desired strength, which may, for example, resist undesired deformation, bending, flexing, ripping, warping, sagging, cracking, and/or any other process where surface and/or physical properties of the material may change the ability to affect a reproducibly accurate needle bend, and/or the like. In some implementations, each of the housing sections 111 and 131 and the coupling element 121 can be formed from the same material(s). In other implementations, at least one of the first housing section 111, the second housing section 131, and/or the coupling element 121 can be formed from different material(s). For example, in some embodiments, the second housing section 131 may be formed from a relatively strong or relatively hard material and/or may be otherwise reinforced to resist undesired deformation, bending, flexing, ripping, puncturing, etc. as a result of contact with a portion of the needle 101 during a needle bending operation, while the coupling element 121 may be formed from a relatively soft or flexible material that allows for a desired amount of bending, flexing, etc. during the needle bending operation, as described in further detail herein.

In some embodiments, the needle bending assembly 102 or sections, elements, and/or portions thereof can be formed of a material that allows for elastic or non-permanent deformation and/or bending while resisting or otherwise limiting plastic or permanent deformation and/or bending. For example, in some instances, the needle bending assembly 102 can be manipulated from an initial or undeformed state to a bent, rotated, and/or reconfigured state to bend a portion of the needle 101 disposed therein and then can be allowed to return (substantially) to the same initial or undeformed state after the needle 101 is bent.

In some implementations, the needle bending assembly 102 may be fabricated via injection molding using any suitable material (e.g., plastic). Furthermore, the needle bending assembly 102 or at least a portion of the coupling element 121 may utilize and/or form a living hinge configured to elastically (non-permanently) deform to allow movement of the second housing section 131 relative to the first housing section 111, as described in further detail herein. In some cases, such a configuration can allow the needle bending assembly 102 to be unitarily or monolithically formed, which in turn, can simplify manufacturing, etc. In some cases, the needle bending assembly 102 and/or the coupling element 121 can include a mechanical hinge or other movable, bendable, and/or flexible element that is formed at least in part by an outwardly facing convexity, bump, etc. on the first housing section 111, and a matching inwardly facing concavity, dimple, etc. on the second housing section 131 (or vice versa).

In some cases, injection molding can be used to separately form parts of the needle bending assembly 102 (e.g., the first and the second housing sections 111 and 131 may be fabricated separately), which are subsequently joined, coupled, attached, etc. For example, the sections 111 and 131 may be separately formed (e.g., via injection molding) and may be joined via the coupling element 121 (e.g., at least a portion of which may form a living hinge) in a subsequent manufacturing process such as, for example, an over-molding process and/or a joining or coupling process such as an adhesive process, a welding process (e.g., ultrasonic welding), and/or the like. In some other cases, bottom portions of the first and the second housing sections 111 and 131 with the coupling element 121 (e.g., forming a living hinge or the like) therebetween may be fabricated as a single part, while top covers or portions of the first and the second housing sections 111 and 131 may be fabricated separately and connected via suitable connecting elements (e.g., clamps, fasteners, etc.) or via suitable connecting processes (e.g., ultrasonic welding or other connecting or joining processes) to the corresponding bottom portions of the first and the second housing sections 111 and 131.

A non-limiting list of materials from which the needle bending assembly 102 can be formed can include, for example, metals, metal alloys, woods, glasses, ceramics, polymers, and/or the like. In some embodiments, the needle bending assembly 102 (or portions or sections thereof) can be formed from biocompatible materials, which may be selected based on one or more properties of the constituent material such as, for example, stiffness, toughness, durometer, bioreactivity, etc. Non-limiting examples of suitable biocompatible metals can include pharmaceutical grade stainless steel, gold, titanium, nickel, iron, platinum, tin, chromium, copper, and/or alloys thereof. Non-limiting examples of suitable biocompatible polymer materials can include polylactides, polyglycolides, polylactide-co-glycolides, polyethylene-glycols, polyanhydrides, polyorthoesters, polyetheresters, polycaprolactones, polyesteramides, poly(butyric acid), poly(valeric acid), polyurethanes, polyamides (nylons), polyesters, polycarbonates, polyacrylates, polystyrenes, polypropylenes, polyethylenes, polyethylene oxide, polyolefins, polyethersulphones, polysulphones, polyvinylpyrrolidones, polyvinyl chloride, polyvinyl fluoride, poly(vinyl imidazole), polyether urethanes, polyether urethanes, polyetheretherketones (PEEK), polytetrafluoroethylenes (PTFE), polylactones, chlorosulphonate polyolefins, ethylene-vinyl acetates and other acyl substituted cellulose acetates, elastomers, thermoplastics, and/or blends and copolymers thereof. In some implementations, the needle bending assembly 102 can be formed from any of these biocompatible polymer materials using, for example, injection molding (as described above) and/or any other suitable manufacturing process or combination of processes.

The first housing section 111 may be any suitable enclosure or structure containing and/or otherwise defining a first cavity 113 (e.g., a channel, a lumen, or any other space of a suitable shape, size, and/or configuration). FIG. 1B, shows that the first housing section 111 is configured to house and/or at least partially support (e.g., within the first cavity 113) the first needle portion 101A, such that the first needle portion 101A is secured from moving or substantially moving in one or more directions, as indicated by arrows 113s. In some cases, the first needle portion 101A may be secured via one or more inner walls or surfaces of the first housing section 111 that at least partially define(s) the first cavity 113. In some cases, the first needle portion 101A may be secured by one or more protrusions or features that can extend from the inner wall(s) of the first housing section 111 towards the first needle portion 101A. For instance, a protrusion or the like extending from a side wall of the first housing section 111 towards a corresponding side of the first needle portion 101A may be configured to limit or substantially prevent the first needle portion 101A from moving within the first cavity 113 in a direction towards that protrusion or feature. In some embodiments, one or more protrusions can extend on opposite sides of the first needle portion 101A, thereby limiting or substantially preventing the first needle portion 101A from moving in one or more directions along a plane passing through the one or more protrusions (e.g., side-to-side motion).

Similar to the first housing section 111, the second housing section 131 may be any suitable enclosure or structure containing and/or otherwise defining a second cavity 133 (e.g., a channel, a lumen, or any other space of a suitable shape, size, and/or configuration). The second housing section 131 is configured to house and/or at least partially support (e.g., within the second cavity 133) the second needle portion 101B, such that the second needle portion 101B is secured from moving or substantially moving in or more directions relative to or within the second cavity 133 (e.g., at least at or near the distal end portion DE of the needle 101), as indicated by an arrow 133s2 shown in FIG. 1B. Further, optionally, the second housing section 131 may support the second needle portion 101B to limit and/or substantially prevent moving relative to the second cavity 133 at a location indicated by arrow 133s1. In some cases, the second needle portion 101B may be secured via one or more inner walls or surfaces of the second housing section 131 that at least partially define(s) the second cavity 133. In some cases, the second needle portion 101B may be secured by one or more suitable protrusions or features that can extend from the inner wall(s) of the second housing section 131 towards the second needle portion 101B. For instance, a protrusion or the like extending from a side wall of the second housing section 131 towards a corresponding side of the second needle portion 101B (e.g., at a location shown by arrow 133s2) may be configured to limit or substantially prevent the second needle portion 101A from moving within the second cavity 133 in a direction towards that protrusion or feature. In some embodiments, one or more protrusions can extend on opposite sides of the second needle portion 101B, thereby limiting or substantially preventing the second needle portion 101B from moving in one or more directions along a plane passing through the one or more protrusions (e.g., side-to-side motion).

The first housing section 111 and the second housing section 131 are coupled via the coupling element 121. The coupling element 121 can be any suitable element for allowing a movement of the second housing section 131 relative to the first housing section 111 while maintaining an attachment to the first housing section 111. As shown in FIGS. 1B and 1C, the arrangement of the needle bending assembly 102 is such that a third needle portion 101C is disposed or positioned between the first housing section 111 and the second housing section 131. In some embodiments, the third needle portion 101C can be disposed in a position corresponding to the coupling element 121. For example, although not shown in FIGS. 1B and 1C, in some implementations, the coupling element 121 can be in contact with a least a part of the third needle portion 101C, as described in further detail herein.

FIG. 1B shows the needle bending assembly 102 in a first configuration in which the second housing section 131 is substantially aligned with the first housing section 111, while FIG. 1C shows the needle bending assembly 102 in a second configuration in which the second housing section 131 is rotated (e.g., clockwise, as indicated by arrow 134) about an into-the-page axis X1 passing through the coupling element 121. In such an embodiment, the coupling element 121 may be a suitable hinge (e.g., living hinge) or a flexible connecting element (e.g., the flexible connecting element may be a plastic strip, rubber strip, fiber glass strip, fabric strip, and the like). In some cases, the coupling element 121 may have groves, indentations, convexities, concavities, bumps, dimples, and/or any other structural elements facilitating bending of the coupling element 121 at a particular location of the coupling element 121. It should be noted that the coupling element 121 implemented as a hinge or a flexible connecting element is only one possible embodiment, and other connecting or coupling elements may be used. For instance, the coupling element 121 may be a ball joint connector, mechanical hinge, and/or any other suitable connecting element (e.g., the coupling element 121 may be a combination of several connecting elements such as a combination of hinges, flexible elements, and the like).

The coupling element 121 may be configured to allow a selected range of motion for the second housing section 131. For example, the coupling element 121 may allow the second housing section 131 to rotate by, to, and/or through a selected angle (e.g., about 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 16 degrees, 17 degrees, 18 degrees, 19 degrees, 20 degrees, or more). In some embodiments, the selected angle can be about 5 degrees. In some embodiments, the coupling element 121 may be configured to allow the second housing section 131 to rotate by or to at least one selected angle from a selected range of angles (e.g., a selected range of angles between 1 degree and 20 degrees). In some embodiments, the selected angle can include a degree or amount of overbending based at least in part on the needle 101 at least partially rebounding, relaxing, and/or partially straightening when a force that causes the bending is removed. For example, in some embodiments, the second housing section 131 can be allowed to rotate by about 6 degrees relative to the first housing section 111, which can slightly overbend the needle 101 to result in a final 5 degree bend after the needle 101 rebounds, relaxes, and/or partially straightens. While described as a 1 degree of overbending, it should be understood that the degree of overbending can be greater or less than 1 degree and can be at least partially based on one or more characteristics or physical properties of the needle 101.

In some cases, the coupling element 121 may allow the second housing section 131 to rotate by a predetermined and/or preselected angle, and in other cases, the angle or amount of rotation may be selected (herein referred to as dialed) by a user, as further described below. In some cases, when the coupling element 121 includes more than one connecting element, movement of each connecting element may be controlled independently by a user.

As shown in FIG. 1C, the movement of the second housing section 131 (e.g., rotation of the second housing section 131 by or through a selected angle about the axis X1) results in a bending of the needle 101. For example, in some embodiments, the needle 101 can be configured to bend at or along the third needle portion 101C for at least the reason that it is not supported by the inner walls (or protrusions, features, etc.) of the first housing section 111 and/or the second housing section 131, as described above with reference to the first needle portion 101A and the second needle portion 101B, respectively. In some embodiments, at least a portion of the coupling element 121 can be reconfigured, moved, deformed, bent, etc. to allow the second housing section 131 to be moved or rotated relative to the first housing section 111. Moreover, the coupling element 121 can be in contact with the third needle portion 101C such that this reconfiguring, moving, deforming, bending, etc. results in the coupling element 121 exerting a force on the third needle portion 101C operable to bend the needle 101 at or along the third needle portion 101C.

The needle 101 contains a lumen oriented axially and extending throughout the needle 101 (e.g., the lumen may extend continuously through each of the proximal end portion PE and the distal end portion DE of the needle 101). The lumen may be used for delivering fluids to a patient, removing fluid (or tissue for biopsy purposes) from the patient, and/or otherwise allowing access to an internal portion of the patient (e.g., a human patient or a non-human patient such as an animal). In some implementations, during a needle bending procedure, an indwelling stylet (e.g., a thin wire) may be disposed in the lumen to ensure the structural stability of the lumen (e.g., to ensure that the lumen does not collapse or kink at the third needle portion 101C during the bending procedure). In some cases, the stylet may be made from a material that has a modulus of rigidity that is comparable to the modulus of rigidity of the metal forming the needle. For instance, the stylet may be made from the same (or similar) material as the material of the needle 101. In some cases, the stylet extending through the lumen of the needle 101 may be made from several different segments, with each segment having selected elastic properties. For example, the stylet may have first segment corresponding to a first needle portion 101A, a second segment corresponding to the second needle portion 101B, and a third segment corresponding to the third needle portion 101C. In some cases, the stylet may include a friction reducing coating (e.g., the coating may be a fluoropolymer such as Teflon °, and the like) to ease the withdrawal of the stylet from the lumen of the needle 101 after the needle 101 is bent.

In some implementations, a stylet or the like need not be disposed in the lumen of the needle 101 for bending. For example, in some embodiments, the needle 101 can be formed from a material and/or can have one or more characteristics configured to limit and/or substantially prevent kinking of the needle 101. In some implementations, to ensure that the lumen does not collapse (or deform) during the bending procedure, a degree of curvature at the bent portion of the needle 101 (e.g., along the third needle portion 101C) may be maintained below a maximum threshold value. The curvature of the bent portion of the needle 101 (e.g., along the third needle portion 101C) may be based at least in part on a length of the third needle portion 101C, which in turn, can be controlled by and/or based at least in part on a distance separating the first housing section 111 and the second housing section 131. In embodiments in which the coupling element 121 contacts the third needle portion 101C to bend the needle 101, the curvature of the bend along the third needle portion 101C can be based at least in part on a shape of a portion of the coupling element 121 that contacts the third needle portion 101C. For example, in some embodiments, the coupling element 121 can be configured to deform when the second housing section 131 is rotated such that a relatively broad surface of the coupling element 121 contacts the third needle portion 101C, which in turn, results in a distribution of the force exerted by the coupling element 121 over a sufficiently long portion of the needle 101 to gradually bend the needle 101 rather than, for example, kinking or abruptly bending the needle 101.

In some embodiments, the coupling element 121 can be configured to deform in or along multiple places when the second housing section 131 is rotated such that a desirable surface at or along each place of the coupling element contacts a desirable place or segment of the third needle portion 101C. In such embodiments, the contact at multiple places along the third needle portion 101C can act and/or can provide multiple fulcrums about which the needle 101 is bent, which in turn, can allow the needle 101 to be bent to a greater degree, angle, and/or extent than may otherwise result from a single point of contact (or single fulcrum about which the needle 101 is bent). In some such embodiments, a size, length, and/or configuration of at least the coupling element 121 can be selected based at least in part on the desirable number and/or position of deformation points along the coupling element 121, thereby allowing the needle 101 through any suitable angle.

FIGS. 2-18 show various views of an example embodiment of a needle bending system 200 having a needle bending assembly 202, which includes a first housing section 211, a second housing section 231, and a coupling element 221. Various sections, cavities, components, etc. of the needle bending system 200 may be similar to the respective sections, cavities, components, etc. of the needle bending system 100. For example, the housing sections 211 and 231 may be similar in at least form and/or function to the respective housing sections 111 and 131, as shown in FIGS. 1A-1C. The first housing section 211 and the second housing section 231 are connected by the coupling element 221, which may be similar in at least form and/or function to the coupling element 121 of the needle bending system 100. The first housing section 211 defines a first cavity 213, and the second housing section 231 defines a second cavity 233, which may be similar in at least form and/or function to the first cavity 113 and the second cavity 133, respectively.

Figure 2:
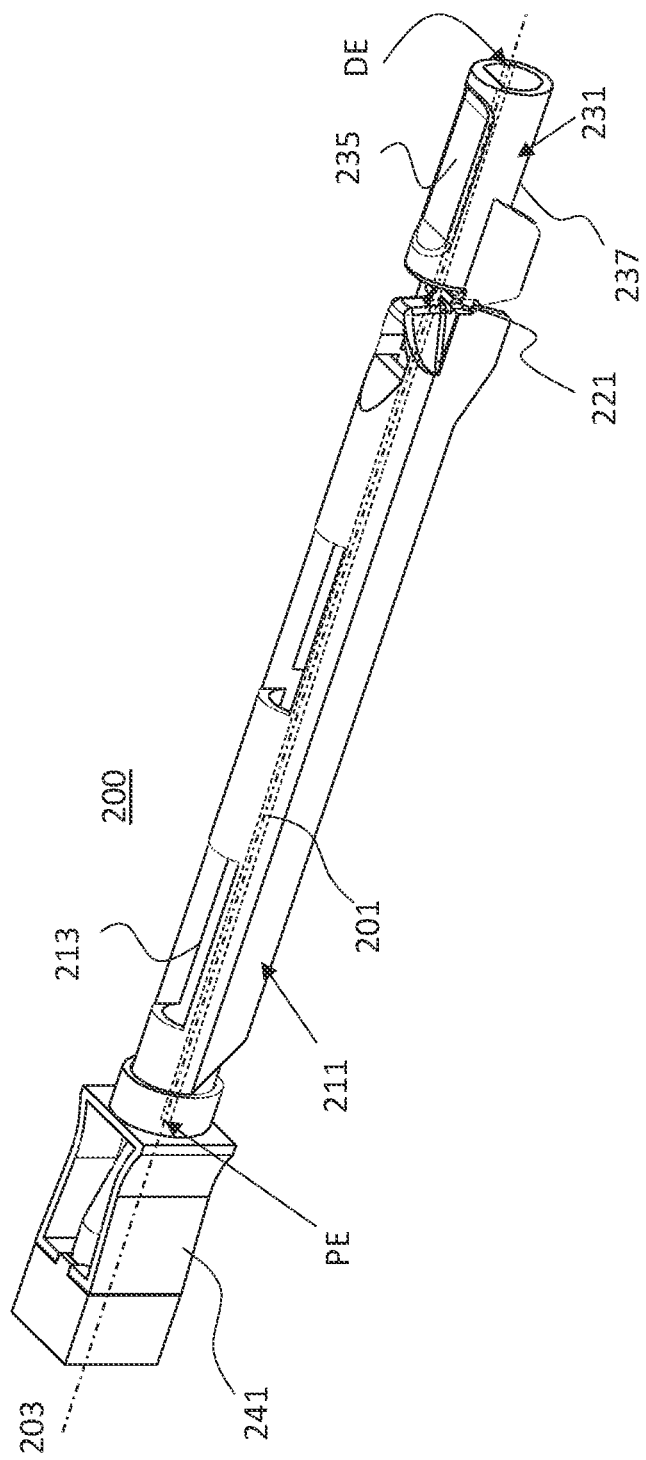
Figure 3:
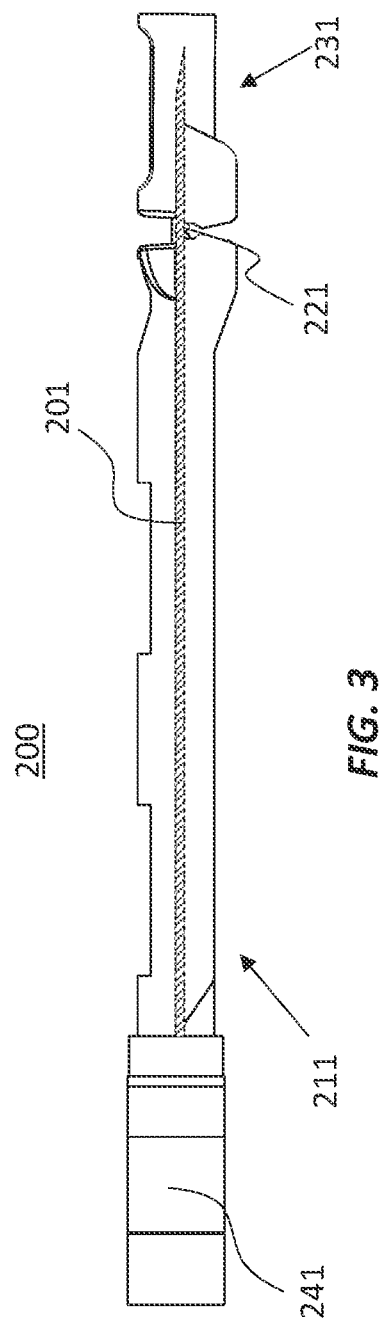

FIGS. 2-7 show the needle bending system 200 in a first configuration with an unbent needle 201 housed in the first and the second housing sections 211 and 231. More specifically, FIG. 2 shows an isometric view of the needle bending system 200 showing the needle bending assembly 202 housing the needle 201. FIGS. 3 and 4 are a side view and a top view, respectively, of the needle bending system 200. FIG. 5 is a cross-sectional view of the needle bending system 200 taken along a line 5-5 defining a cross-sectional plane, as indicated in FIG. 4. FIG. 6 is an enlarged view of a portion of the needle bending system 200 identified in FIG. 5. FIG. 7 is a rear view of the needle bending system 200.

Although not shown, the needle bending system 200 can also include a stylet, which can be disposed within a lumen of the needle 201. In some implementations, the stylet can be disposed within the needle 201 during a bending operation such that both the needle 201 and the stylet are bent in or by the same process. Alternatively, in some implementations, the stylet can be disposed in the lumen of the needle 201 during insertion into a patient and then can be removed from the needle 201 prior to a bending operation. At a proximal end portion PE, the needle 201 is connected to and/or includes a needle hub 241. Although not shown, the needle hub 241 can also be connected (at least temporarily) to a stylet hub allowing for collective and/or independent control of the needle 201 and/or the stylet relative to the needle bending assembly 202. A distal end portion DE of the needle 201 is located within the second housing section 231. The needle hub 241 may be used by a medical professional (e.g., a physician, surgeon, etc.) to rotate, move, advance, remove, etc. the needle 201. For example, the medical professional can use the needle hub 241 to remove the needle 201 from the needle bending assembly 202 (e.g., after performing a bending process). In some implementations, the needle hub 241 and/or a portion thereof can be at least partially disposed in the first housing section 211 of the needle bending assembly 202 when the needle 201 is disposed therein. In some embodiments, a proximal end portion of the first housing section 211 can be sized and/or shaped in a manner that allows a distal end portion of the needle hub 241 to be disposed therein (see e.g., FIG. 5).

FIG. 2 further shows at least the second housing section 231 having and/or forming one or more shapes, surfaces, features, etc., configured to enhance and/or facilitate ergonomics of the needle bending assembly 202 (e.g., at least during a needle bending process). For example, a top side or surface of the second housing section 231 can include and/or form an indentation 235 and/or any other suitable feature that can enhance and/or facilitate the ergonomics associated with a user griping the second housing section 231. Similarly, a bottom side or surface 237 may be shaped, sized, and/or configured in such a way to enhance and/or facilitate the ergonomics associated with the user gripping the second housing section 231 (e.g., the bottom side or surface 237 also may have and/or form an indentation or any other suitable feature (not shown)). In some instances, during use, a user (e.g., a medical professional) may pinch, grasp, hold, and/or otherwise engage the second housing section 231 by placing one or more fingers of a first hand on the indentation 235 of the top side or surface and on the bottom side or surface 237, while holding the first housing section 211 with a second hand. In some instances, the presence of the indentation 235 may guide the placement of the user's finger(s) of the first hand on the top surface of the second housing section 231, while the user's thumb of the first hand engages and/or contacts the bottom side or surface 237 of the second housing section 231 (or vice versa). As described in further detail herein, such an arrangement can facilitate the user in manipulating the needle bending assembly 202 to, for example, rotate the second housing section 231 relative to the first housing section 211, thereby bending needle 201 housed therein. Although not shown in FIGS. 2-7, in some embodiments, the indentation 235 can include and/or form one or more features or can have a surface finish or the like configured to enhance a user's grip of the second housing section 231. For example, the indentation 235 can include one or more protrusions, ridges, channels, and/or the like and/or can have a knurled and/or otherwise textured finish. Similarly, the bottom side or surface 237 also can have any suitable feature and/or surface finish.

When the needle bending system 200 is in the first configuration, the housing sections 211 and 231 are aligned or substantially aligned such that a longitudinal axis 203 of the needle bending assembly 202 extends through each of the housing sections 211 and 231. For example, as shown in FIG. 5, the first cavity 213 and/or portions thereof can be a lumen or other opening that extends along a first central axis and the second cavity 233 and/or portions thereof can be a lumen or other opening that extends along a second central axis, where the alignment of the housing sections 211 and 231 is such that the first central axis is coaxial to the second central axis. Moreover, the first central axis and the second central axis can be substantially aligned or coaxial with the longitudinal axis 203. The needle 201 can be disposed in and/or can extend at least in part through the housing sections 211 and 231 such that a central (longitudinal) axis of the needle 201 is substantially aligned or coaxial with the longitudinal axis of the needle bending assembly 202.

As shown in FIGS. 5 and 6, the first housing section 211 includes a set of inner walls that define the first cavity 213. As described above with reference to the needle bending assembly 102, the inner walls can be configured to contact and/or can include one or more features configured to contact a first needle portion 201A (or at least parts thereof) disposed in the first housing section 211, which in turn, can support the first needle portion 201A to limit and/or substantially prevent undesirable movement, bending, flexing, etc. of at least a portion of the needle 201. Similarly, the second housing section 231 includes a set of inner walls that define the second cavity 233 that receives and/or at least temporarily houses a second needle portion 201B. In some embodiments, the second cavity 233 can have and/or can be defined to have a diameter D2 which is sufficiently large to allow the second cavity 233 to house the second needle portion 201B of the needle 201, even when the needle 201 is bent. Moreover, in some implementations, the arrangement of the inner walls of the second housing section 231 can be such that transitioning the needle bending system 200 from the first configuration toward a second configuration places a portion of the inner walls in contact with the second needle portion 201B, thereby facilitating bending of the needle 201, as described in further detail herein.

FIG. 6 shows further details of the coupling element 221 and shows a first shoulder 212 included in and/or formed by the first housing section 211 and a second shoulder 232 included in and/or formed by the second housing section 231. The coupling element 221 can be any suitable coupler or the like that can allow the second housing section 231 to be moved, rotated, and/or reconfigured relative to the first housing section 211. In some implementations, the first shoulder 212 and the second shoulder 232 can be configured to at least partially define and/or control a degree and/or angle associated with the bending or rotating of the second housing section 231 relative to the first housing section 211. Said another way, the coupling element 221 can allow and/or enable movement, rotation, and/or reconfiguration of the second housing section 231 relative to the first housing section 231 and the shoulders 212 and 232 can at least partially define an extent, degree, angle, and/or range of motion associated with that movement, rotation, and/or reconfiguration.

For example, FIG. 6 shows a point or surface 216 of the first shoulder 212 and a point or surface 236 of the shoulder 232, which are brought or configured to be brought into contact when the second housing section 231 is bent relative to the first housing section 211. The points or surfaces 216 and 236 can be, for example, the closest separated points or surfaces of the shoulders 212 and 232, and the distance between these points or surfaces 216 and 236 can at least partially determine, define, and/or control a range of motion through which the second housing section 231 can be rotated relative to the first housing section 211. In some instances, for example, the rotation of the second housing section 231 can be stopped and/or limited in response to the point 216 coming into contact with the point 236. In some instances, for example, a user can exert a force that is sufficient to rotate the second housing section 231 relative to the first housing section 211 (e.g., a force sufficient to deform the coupling element 221 and bend the needle 201). In general, the user can exert the force to rotate the second housing section 231 through the predetermined angle or range of motion until the surfaces 216 and 236 of the shoulders 212 and 232 are brought into contact. The contact between the surfaces 216 and 236, in turn, resists further rotation of the second housing section 231, which can be felt by the user because the same amount of applied force no longer rotates the second housing section 231 relative to the first housing section 211. Said another way, the contact between the surfaces 216 and 236 can result in a hard stop or limit to the bending process, which the user may perceive as a notable increase in resistance to further rotation of the second housing section 231.

It should be noted that the shoulder 212 and/or the shoulder 232 may have any suitable size and shape, which may be selected based on a desired amount or angle of rotation of the second housing section 231 relative to the first housing section 211. Said another way, the shoulders 212 and/or 232 can be sized and/or shaped based at least in part on a desired amount or angle of bending of the needle 201. In an example embodiment, the shoulders 212 and/or 232 may be or may include a set of protrusions extending from the first and second housing sections 211 and/or 231, respectively. For instance, as shown in FIG. 7, the first shoulder 212 may form two protruding elements at the bottom portion of the first housing section 211. In some implementations, both shoulders 212 and 232 may be implemented as protrusions at bottom portions of the respective first and second housing sections 211 and 231. In some embodiments, the shoulders 212 and 232 can be similar or substantially the same in at least size and/or shape. In such embodiments, for example, at least the portions of the shoulders 212 and 232 that form or include the points or surfaces 216 and 236, respectively, can be similar in size and/or shape. In other embodiments, the shoulders 212 and 232 can be sized and/or shaped differently and/or at least the points or surfaces 216 and 236 can be sized and/or shaped differently. In some such embodiments, the size, shape, and/or configuration or the first shoulder 212 and the second shoulder 232 can be selected to result in rotation of the second housing section 231 relative to the first housing section 211 with a desired set of characteristics, such as, for example, an amount of force needed to rotate the second housing section 231 a desired amount, and/or the like.

As described above, the coupling element 221 can be and/or can include any suitable coupler or connector configured to attach the second housing section 231 to the first housing section 211. In some embodiments, for example, the coupling element 221 can be and/or can form a living hinge or the like that can attach the housing sections 211 and 231 while allowing the second housing section 231 to be moved, rotated, and/or otherwise reconfigured relative to the first housing section 211. As described above with reference to the coupling element 121, the coupling element 221 shown in FIGS. 5 and 6 can be any suitable size and/or shape, and/or can include any suitable feature or the like that can at least partially define, determine, and/or control one or more characteristics associated with a bending or flexing of the coupling element 221. In some embodiments, for example, the coupling element 221 can include and/or can form one or more discontinuities, protrusions, ridges, channels, slits, etc. that can facilitate a bending and/or flexing of the coupling element 221. In some embodiments, the coupling element 221 can include an engineered characteristic, feature, weakness, and/or the like that can facilitate the bending and/or flexing of the coupling element 221. For example, in some implementations, a discontinuity, weakness, feature, etc. can be formed or included in the coupling element 221 that can at least partially control and/or determine a position or degree of deformation of the coupling element 221 in response to a force exerted to rotate the second housing section 231 relative to the first housing section 211. In other embodiments, the coupling element 221 need not include such a discontinuity, characteristic, feature, etc.

FIGS. 8-13 show the needle bending system 200 in a second configuration where the second housing section 231 has been rotated and/or bent relative to the first housing section 211 to bend the needle 201 housed in the needle bending assembly 202. For example, FIG. 8 is an isometric view of the needle bending system 200 in the second configuration that shows the second housing section 231 rotated about an axis X1 defined by the coupling element 221. FIG. 9 is a side view of the needle bending system 200 in the second configuration that shows the second housing section 231 rotated relative to the first housing section 211 by an angle θ. More specifically, FIG. 9 shows the first central axis 214 extending through the first housing section 211 and the second central axis 234 extending through the second housing section 231, where the angle θ is defined between the axis 214 and the axis 234.

FIG. 10 shows a top view of the needle bending system 200 in the second configuration, and FIG. 11 shows a cross-sectional view of the needle bending system 200 in the second configuration taken along a line 11-11 defining a cross-sectional plane, as indicated in FIG. 10. FIG. 12 an enlarged view of a portion of the needle bending system 200 in the second configuration, identified in FIG. 11. FIG. 13 is a back view of the needle bending system 200 in the second configuration.

FIG. 12 shows that an inner wall 231A of the second housing section 231 is placed in contact with a distal tip 201D of the needle 201 when the second housing section 231 is rotated relative to the first housing section 211. In this manner, a portion of a force exerted on the second housing section 231 that is operable to rotate the second housing section 231 is transferred and/or exerted on the distal tip 201D of the needle 201, which in turn can bend the needle 201 to a desired and/or predetermined angle.

As described above, in some embodiments, the shape, size, and/or configuration of the needle bending assembly 202 can be selected to control one or more characteristics associated with the bending of the needle 201. For example, in some embodiments, one or more characteristics associated with the contact between the inner wall 231A and the distal tip 201D of the needle 201 can be based at least in part on the diameter D2 of the second cavity 233 (or at least a portion thereof), a length of the second needle portion 201B disposed in the second housing section 231, a relative position between the coupling element 221 and the inner wall 231A, and/or the like. In some embodiments, the position of contact along the distal tip 201D of the needle 201 and/or a length of the second needle portion 201B disposed in the second housing section 231 can determine and/or at least partially control a relationship between an amount or angle of rotation of the second housing section 231 and an amount or angle of bending of the needle 201. For example, in some embodiments, increasing a length of the second needle portion 201B disposed in the second housing section 231 may result in an increased amount or angle of bending of the needle 201 relative to a shorter length. Moreover, in some embodiments, the length of the second needle portion 201B and/or one or more characteristics of the inner wall 231A can be selected to reduce a likelihood of the distal tip 201D puncturing the second housing section 231 and/or to reduce a likelihood of the distal tip 201D being damaged by the contact with the inner wall 231A.

The shape, size, and/or configuration of the needle bending assembly 202 can be selected based on a length, and/or width of the needle 201. For instance, some known spinal needles may have length of a few inches (e.g., 3.5 inches, 5 inches, 7 inches, and/or the like), and the length of the first housing section 211 (and/or the second housing section 231) may be selected based on that length. As shown, a length of the first housing section 211 is shorter than the length of the needle 201 and thus, may be varied based at least in part on a length of the needle 201. In an example embodiment, the length of the first housing section 211 may be shorter than the length of the needle 201 by 0.5 inches, by 1 inch, by 1.5 inches, by 2 inches, by 2.5 inches, by 3 inches, by 3.5 inches, and/or the like or any length or fraction of a length therebetween. In some cases, the length of the first housing section 211 may be, for example, 95%, 90%, 85%, 80%, 75%, 70%, 65%, 60%, 55%, 50%, 45%, 40% 35%, 30% or less (or any percentage or fraction of a percentage therebetween) of the length of the needle 201. In some cases, the length of the first housing section 211 may range between 95%-30% of the length of the needle 201, including all the values and ranges in between. Furthermore, by varying a length of the first housing section 211 based on a length of the needle 201, a location along the needle 201 that is aligned with and/or that corresponds to the coupling element, and a length of the distal end portion DE of the needle 201 disposed in the second housing section 231 may be varied, adjusted, tuned, selected, etc. In this manner, a location along the needle where the bend is formed and/or a degree or amount of bending imparted on the needle 201 can be varied, adjusted, tuned, selected, etc.

The cross-sectional shape and/or area of the first and/or second cavity 211 and/or 213 (or at least portions thereof) also may be based at least in part on a gauge of the needle 201. For example, the cross-sectional area of the first cavity 213 and/or the second cavity 233 may be selected to have a shape and/or size, at least at some locations along the longitudinal axis 203, based at least in part on a gauge or cross-sectional area of the needle 201 that can allow the needle 201 to be supported within the first and second housing section 211 and 231, while also allowing the needle 201 to be bent and withdrawn from the needle bending assembly 202.

In some embodiments, one or more characteristics, aspects, features, etc. of the coupling element 221 can be selected to facilitate bending of the needle 201 in a desired and/or predetermined manner. For example, FIG. 12 shows the coupling element 221 in contact with a third needle portion 201C disposed between the first housing section 211 and the second housing section 231. At least a portion of the coupling element 221 can deform and/or deflect as the coupling element 221 allows the second housing section 231 to be rotated relative the first housing section 211. In some implementations, the deformation and/or deflection can be controlled and/or directed (e.g., based on one or more features or characteristics of the coupling element 221) such that a portion of the coupling element 221 is pushed into and/or in the direction of the third needle portion 201C which in turn, exerts a force along the third needle portion 201C. As such, when at least a portion of the force used to rotate the second housing section 231 is transferred to the distal tip 201D of the needle 201, the coupling element 221 (or the force exerted by the coupling element 221) can act and/or provide a fulcrum about which the third needle portion 201C can be bent.

In some embodiments, one or more characteristics, aspects, features, etc. of the needle bending assembly 202 and/or the coupling element 221 can be selected to facilitate bending the needle 201 to or with a specific curvature or characteristics. For example, the needle 201 may be bent such that a portion of the needle 201 (e.g., at or along the third portion 201C of the needle 201) has a constant, gradual, and/or broad curvature at the third portion 201C (e.g., a bend with a relatively large radius of curvature). In some implementations, a curvature of a bend along the third portion 201C of the needle 201 may have and/or may form a gaussian shape as a function of an extent or length of the third portion 201C of the needle 201 (e.g., a length of the portion of the needle 201 disposed between the first and second housing sections 211 and 231). In other implementations, a curvature of the bend along the third portion 201C of the needle 201 may have any other suitable functional dependence of the extent or length of the third portion 201C (e.g., a hat function, a step function, and the like). In some cases, the needle bending assembly 202 can be configured to impart or result in, for example, a dogleg bend or the like at or along the third portion 201C characterized by a relatively sharp bend, such as a bend that has a relatively small radius of curvature (e.g., bent at about 20°, about 30°, about 40°, about 50°, about 60°, about 70°, about 80°, about 90° or any other suitable angle and with a relatively small radius of curvature). In some implementations, the bend formed along the third portion 201C can be based at least in part on a type of needle or a procedure in which the bent needle 201 will be used. For example, in some instances, it may be desirable to form a bend having a relatively large and constant radius of curvature when the needle 201 is intended for use in a biopsy procedure (e.g., the needle 201 is a biopsy needle), as the relatively large or broad arc of the bend may allow for easier passage into target tissue being sampled.

In some embodiments, one or more characteristics, aspects, features, etc. of the needle bending assembly 202 can be selected to facilitate or impart an overbending of the needle 201. For example, "overbending" can refer to a process of bending the needle 201 by an angle or by an amount that is larger or more than a desired angle or amount based on a determined and/or anticipated relaxation of a portion of the needle 201 to the desired target bend angle or amount. In some implementations, the amount of relaxation can be determined based on one or more properties of the needle 201 such as, for example, elasticity, flexibility, hardness, toughness, etc. of the constituent material of the needle 201). In some implementations, for example, the needle 201 can be overbent by about 0.5%, 1.0%, 1.5%, 2.0%, 2.5%, 3.0%, 3.5%, 4.0%, 4.5%, 5.0%, 10%, 15%, 20%, or any percentage or fraction of a percentage therebetween. In some implementations, the needle 201 can be over bent by less than 0.5% or more than 20%.

In some embodiments, the second housing section 231 can be configured to at least partially stabilize the needle 201 during the bending process, which in turn, can facilitate control of the bending of the needle 201. For example, FIG. 12 shows that a wall of the second housing section 231 (e.g., adjacent the coupling element 221) defines an opening 231B through which the needle 201 can extend to allow the second needle portion 201B to be disposed in the second housing section 231. In some embodiments, a size, shape, position, and/or configuration of the opening 231B can be selected such that one or more surfaces of the wall defining the opening 231B engage and/or contact a surface of the needle 201. In this manner, the contact between the one or more surfaces defining the opening 231B and the surface of the needle 201 can act to stabilize at least the second needle portion 201B relative to the second housing section 231. Thus, when the second housing section 231 is rotated relative to the first housing section 211, the forces exerted on the needle 201, the points along the needle 201 at which the forces are applied, and/or any other selectable, adjustable, tunable, or desired aspects or features of the needle bending system 200 can collectively control the manner and/or degree of bending imparted on the needle 201. Moreover, such arrangements, features, aspects, etc. can allow bending of the needle 201 in a desired, predictable, and repeatable manner.

Figure 14:
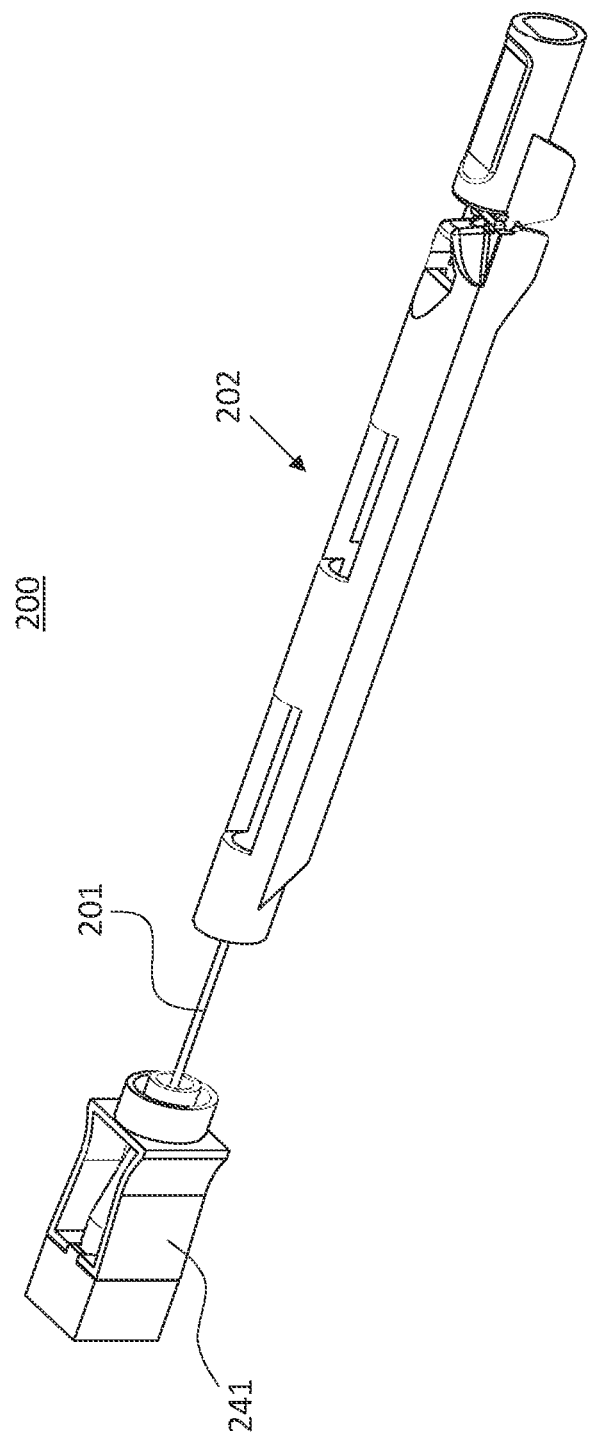

FIGS. 14-18 show the needle bending system 200, as the needle 201 is withdrawn from the needle bending assembly 202 (e.g., after bending the needle 201). FIG. 14 is an isometric view of the needle bending system 200, FIG. 15 is a side view of the needle bending system 200, and FIG. 16 is a top view of the needle bending system 200. FIG. 17 shows a cross-sectional view of the needle bending system 200 as the bent needle 201 is being withdrawn, taken along a line 17-17 defining a cross-sectional plane, as indicated in FIG. 16. In some embodiments, the arrangement of the needle bending assembly 202 can be such that after the needle 201 is bent, the needle bending system 200 can be transitioned from the second configuration to a third configuration. In the third configuration, the needle bending system 200 can be in a state and/or configuration that is similar to or substantially the same the first configuration but the needle 201 disposed in the needle bending assembly 202 is now bent. In other words, in some embodiments, the second housing section 231 can return to its unmoved or non-rotated position relative to the first housing section 211. As shown in FIGS. 14 and 15, the needle 201 is withdrawn from the needle bending assembly 202 via the needle hub 241, which in turn, allows the bent needle 201 to be used for a medical procedure. FIG. 17 shows the needle 201 withdrawn from the second housing section 231 and partially withdrawn from the first housing section 211. As described above, the size, shape, and/or configuration of the first cavity 213 and the second cavity 233 can be such that the needle 201 can be moved (e.g., along or relative to the longitudinal axis 203 of the needle bending assembly 202) after being bent. For example, FIG. 18 is an enlarged view of a portion of the needle bending system 200, identified in FIG. 17, showing the needle 201 withdrawn from the second housing section 231. As shown, the first cavity 213 having a diameter D1 that is sufficiently large such that the bent needle 201 can pass through the first cavity 213, as the bent needle 201 is being pulled out of the needle bending assembly 202.

Figure 19:
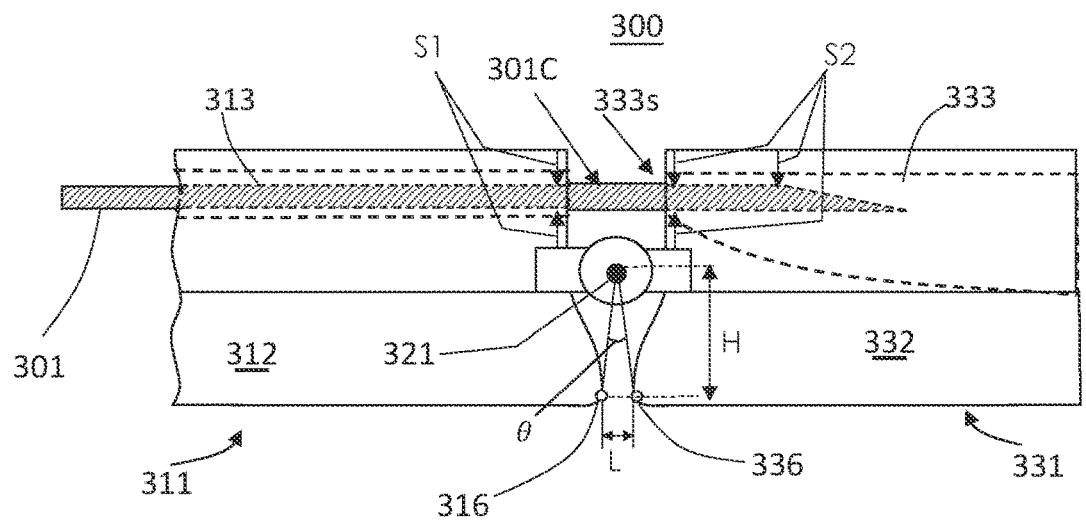
FIG. 19 is a schematic illustration of at least a portion of a needle bending system in a first configuration, according to an embodiment.
Figure 20:
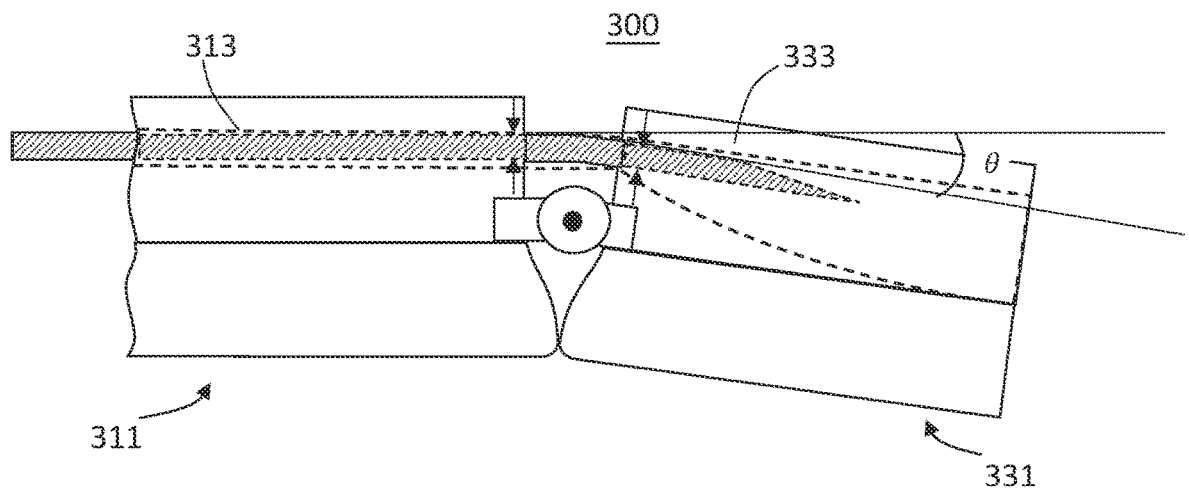

FIGS. 19-24 show an example embodiment of a needle bending system 300 having a first housing section 311 and a second housing section 331. The first housing section 311 defines a first cavity 313, and the second housing section 331 defines a second cavity 333. A needle 301 includes portions that are or can be housed in the first and the second housing sections 311 and 331. Further, a portion 301C of the needle is located between the first and the second housing sections 311 and 331. Various sections, cavities, components, etc. of the needle bending system 300 may be similar to the respective sections, cavities, components, etc. of the needle bending systems 100 and/or 200. FIG. 19 shows the needle bending system 300 in a first configuration with the needle 301 in an unbent configuration being housed in the first and the second housing sections 311 and 313. As shown, at least a portion of the first cavity 313 is aligned with at least a portion of the second cavity 333 allowing the needle 301 to extend therethrough. FIG. 20 shows the needle bending system 300 in a second configuration where the second housing section 331 is rotated relative to the first housing section 311 by an angle θ, which in turn, imparts a bend along a portion of the needle 301 disposed in the needle bending assembly 302.

In some embodiments, the first and the second cavities 313 and 333 can be lumens or the like extending through the first and the second housing sections 311 and 331, respectively. The first and the second housing sections 311 and 331 are connected by a coupling element 321 which, in the example embodiment, is a hinge element. Further, similar to the shoulders discussed above, the first and the second housing sections 311 and 331 include shoulder 312 and 332, respectively. The shoulder 312 is separated from the shoulder 332 by a distance L at points or surfaces 316 and 336, as shown in FIG. 19. In the example embodiment, the points and/or surfaces 316 and 336 are closest points or surfaces between the shoulders 312 and 332. The points or surfaces 316 and 336 are separated (e.g., vertically) from a center of the coupling element 321 by a distance H (as shown in FIG. 19), and lines between the center of the coupling element 321 and the respective points 316 and 336 define an angle θ by which the second housing section 331 may rotate relative to the first housing section 311. In an example embodiment, the angle θ is given by θ=2·a tan(L/2H). Further, as shown in FIG. 19, one or more walls defining the first cavity 313 can support the needle 301 at least at points indicated by arrows S1, while one or more walls defining the second cavity 333 can support the needle 301 at least at points indicated by arrows S2. In this embodiment, the portion 301C of the needle 301 is defined between the points S1 and S2.

In the example embodiment shown in FIGS. 19-24, the second cavity 333 is expanded and/or can otherwise extend in at least one direction (e.g., a vertical direction and/or transverse direction) to provide sufficient space for a portion 301B of the needle 301 after a bending process. For example, FIG. 21 shows the second cavity 333 with the portion 301B of the needle 301 (i) after the needle 301 is bent and (ii) after the second housing section 331 is returned or substantially returned to an unmoved or non-rotated position. In this example, the transverse direction aligns with a coordinate Z (e.g., in and out of the page), the axial direction aligns with a coordinate X, and the vertical direction aligns with a coordinate Y. FIGS. 19, 21, and 23 show that the second housing section 331 has a wall adjacent to the coupling element 321 that defines a slit 333s (e.g., an opening, passage, channel, aperture, etc. that is expanded or extends in the transverse (Z) direction but narrow in the vertical (Y) direction). In some embodiments, this arrangement can be such that the wall defining the slit 333s supports the needle 301 (e.g., at the points indicated by arrows S2, as shown in FIG. 19).

As shown in FIGS. 21 and 22, the second cavity 333 may be in a shape of a half-cylinder with a radius R being larger than a vertical displacement h of the portion 301B of the needle 301 after bending. Such a shape of the second cavity 333 can allow the second housing section 331 to move or rotate relative to the first housing section 311 to bend the needle 301, allow the second housing section 331 to return to a substantially unmoved or substantially non-rotated configuration with the portion 301B of the needle 301 (after bending) disposed in the second cavity 333, and further to allow the needle 301 to be rotated to a sideways orientation, as shown in FIG. 23 (e.g., the needle 301 can be rotated about the X axis in a clockwise or counterclockwise direction). In some implementations, for example, the needle 301 can be rotated about the X axis by 90 degrees, such that the portion 301B of the needle 301 extends in a transverse direction e.g., along the Z axis). Once the needle 301 is rotated as shown in FIG. 23 it can be pulled through the slit region 333s and out of the second cavity 333. As shown in FIG. 24, the first cavity 313 similarly can be defined in the form or shape of a slit (e.g., in the transverse direction) so that the needle 301 may be pulled through that first cavity 313 when the portion 301B is rotated such that it is directed transverse to the first housing section 311.

Figure 25:
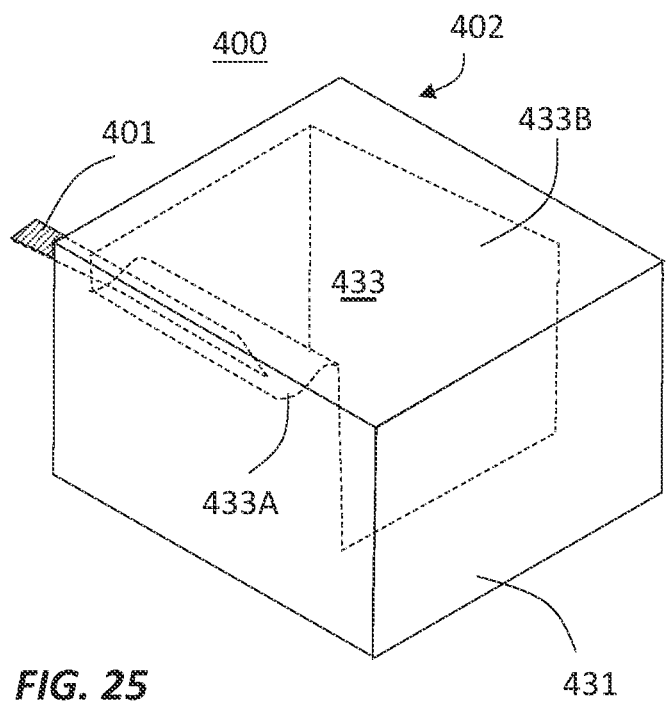
FIGS. 25 and 26 are schematic illustration of a portion of a needle bending system, according to an embodiment.
Figure 26:
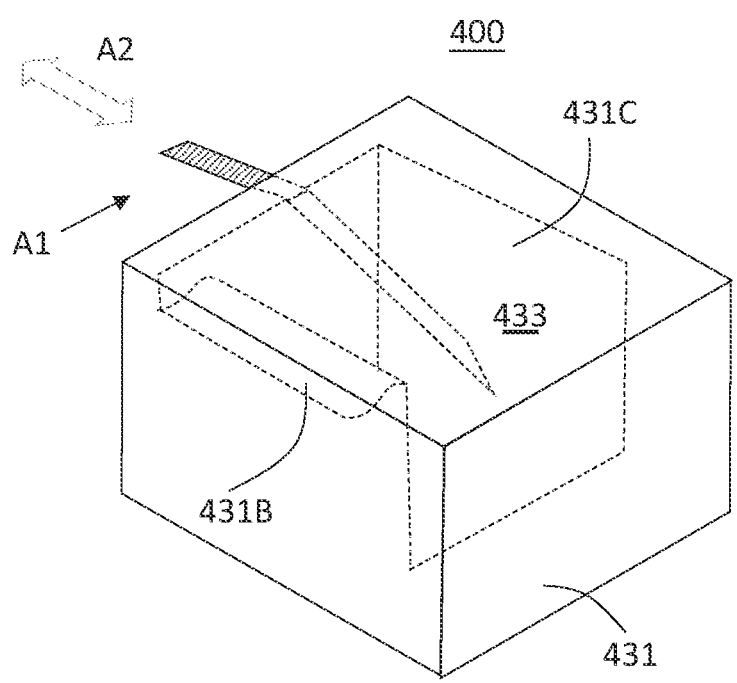

It should be noted that the embodiment shown in FIGS. 19-24 is only one possible embodiment of a needle bending system, and various other embodiments are possible. For example, FIGS. 25 and 26 shows an example embodiment of a needle bending system 400. FIG. 25 shows a second housing section 431 of a needle bending assembly 402 of the needle bending system 400, which defines a second cavity 433 having two regions: a first region 433A and a second region 433B. The first section 433A is configured to house and/or receive a needle 401 prior to bending of the needle 401. After a process of bending the needle 401 (as described above by, for example, rotating the second housing section 431 relative to a corresponding first housing section (not shown in FIGS. 25 and 26)), the needle 401 may be moved in a transverse direction, as indicated by arrow A1, into the second region 433B of the second cavity 433 for subsequent removal from the second housing section 431, as indicated by arrow A2. Note, that a first cavity of the respective first housing section (not shown) may have a similar shape as the second cavity 433 (e.g., the first cavity may also have a first region and a second region which may be similar to the respective first region 433A and the second region 433B). As such, the needle bending system 400 can be used to bend the needle 401 to a desired extent (as described above), and then can allow the needle 401 to be withdrawn from the needle bending assembly 402.

Figure 27:
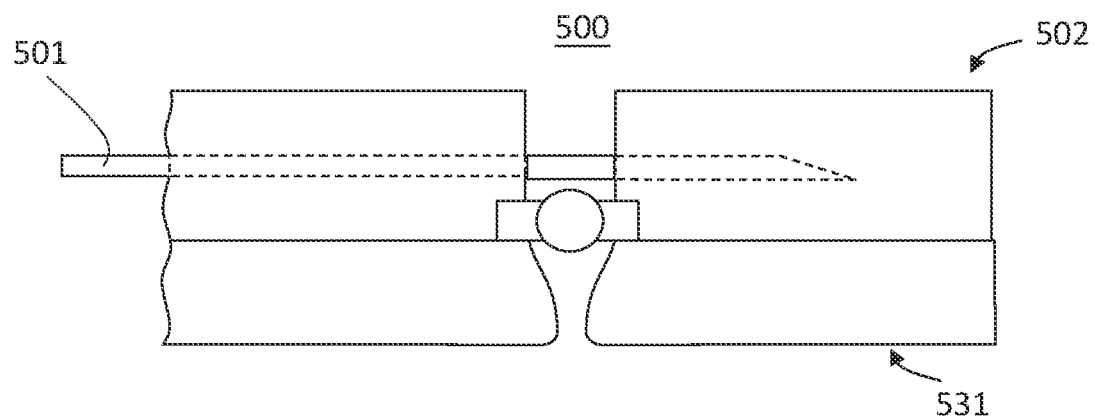
FIGS. 27 and 28 are side view schematic illustration and a top view schematic illustration, respectively, of a portion of a needle bending system, according to an embodiment.
Figure 28:
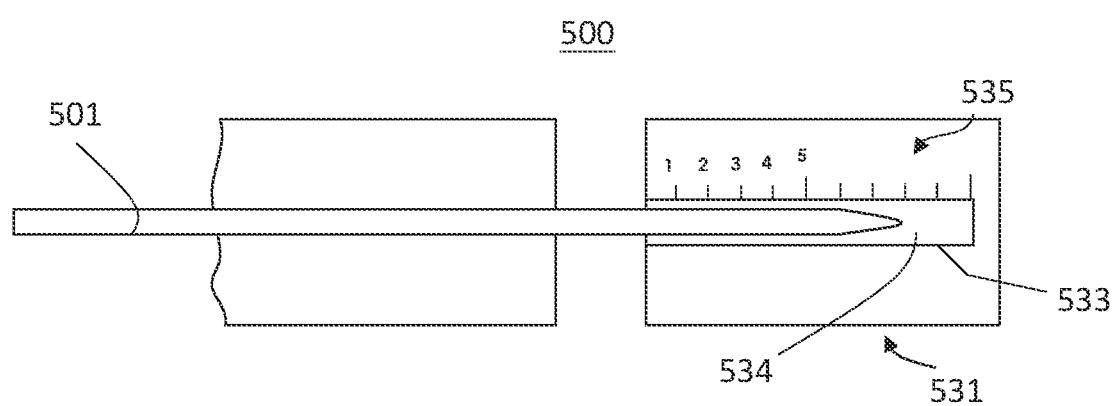

FIGS. 27 and 28 shows another embodiment of a needle bending system 500 having a window for determining a location of a tip of a needle 501 within a second housing section 531 of a needle bending assembly 502. FIG. 27 shows a side view of the needle bending system 500, and FIG. 28 shows a top view of the needle bending system 500.

In this embodiment, a window 534 (or an opening) may be placed, formed, and/or defined at or by a top wall of the second housing section 531 (or at or by any other wall, such as one of side walls, or a bottom wall of the second housing section 531) allowing a user to detect (e.g., visually) a location of the tip of the needle 501 within the second cavity 533. In this example embodiment, the location or depth of the tip of the needle 501 may be determined via ruler or graduated markings 535 (or any other suitable indicia) adjacent to the side the window 534. Having the window 534 with ruler markings 535 (or other indicia) may allow a user to move the needle 501 (e.g., along or in an axial or longitudinal direction) relative to the second cavity 533 prior to bending of the needle 501, thereby allowing the user to select a location of the bend of the needle 501.

Figure 29:
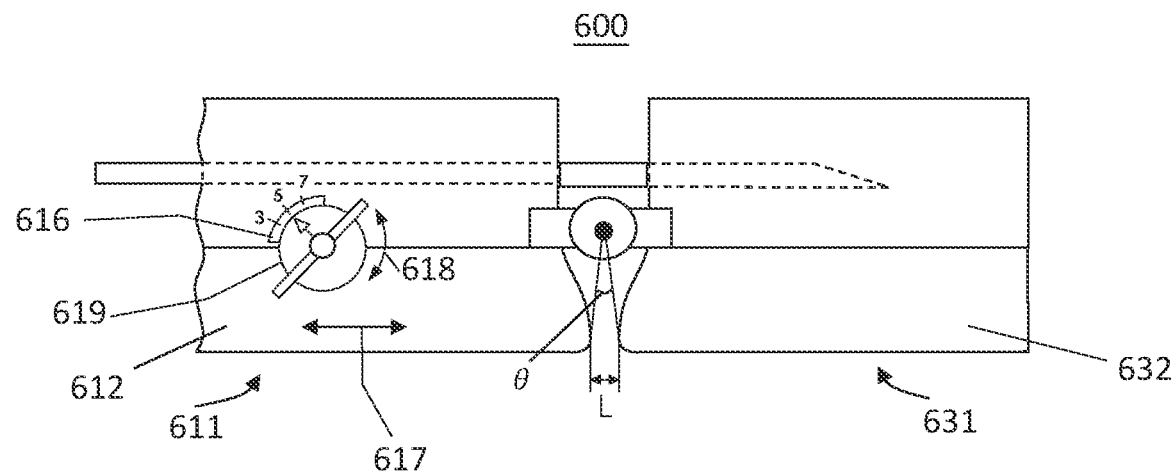
FIGS. 29 and 30 are side view schematic illustrations of a portion of a needle bending system, each according to an embodiment.
Figure 30:
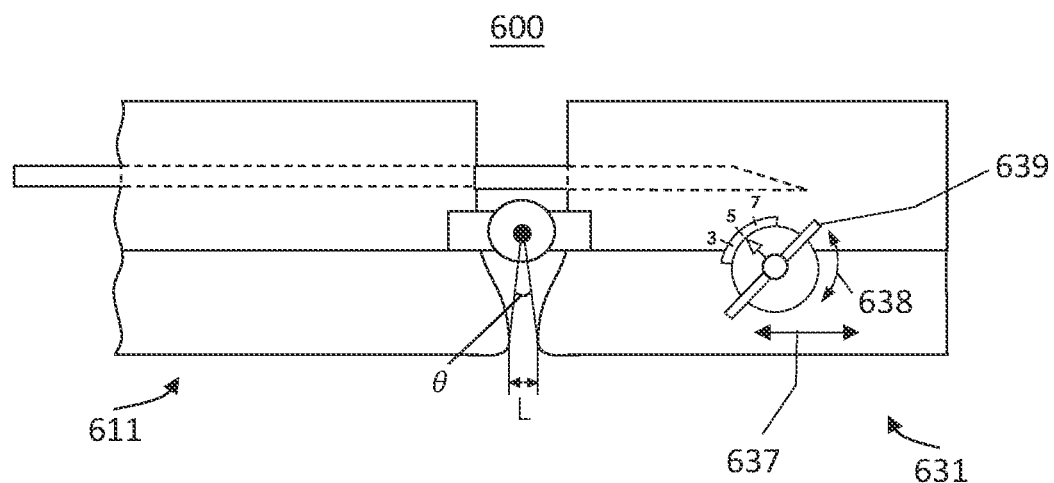

FIGS. 29 and 30 show two implementations of another example embodiment of a needle bending system 600 with additional functionality of adjusting a bend angle θ by adjusting a distance L between a first shoulder 612 of a first housing section 611 and a second shoulder 632 of a second housing section 631. In the example implementation shown in FIG. 29, the first shoulder 612 is configured to move towards or away from the second shoulder 632, as shown by arrow 617. In some instances, the first shoulder 612 may move relative to the first housing section 611, while the first housing section 611 remains in a fixed position relative to the second housing section 631. As shown in FIG. 29, the first shoulder 612 may be configured to be movable via a suitable motion activation mechanism (e.g., via a dial 619 that can be rotated as indicated by arrow 618). In some embodiments, the dial may be adjacent to angular markings 616 (or other indicia) indicating an angle θ that is being selected by rotating dial 619, which in turn, can correspond to an amount of linear movement of the first shoulder 611. For example, the first shoulder 612 may be operably coupled to the first housing section 611 via any suitable coupling mechanisms (e.g., rails, gears, rack-and-pinion, etc.) for linearly moving (e.g., translating) the first shoulder 612 relative to the first housing section 611 in response to rotation of the dial 619 (or any other suitable actuation).

FIG. 30 shows a similar implementation of the needle bending system 600, but with the second shoulder 632 configured to be adjusted by moving the second shoulder 632 as shown by the arrow 637 relative to the second housing section 631 and thus, relative to the first shoulder 612. In this example implementation, the second shoulder 632 can be moved linearly or otherwise translated in response to rotation of a dial 639, as indicated by arrow 638. In other embodiments, the second shoulder 632 can be moved via any suitable activation and/or actuation. While FIGS. 29 and 30 are shown and described as separate implementations, in some embodiments, the implementations can be combined such that each of the first shoulder 612 and the second shoulder 632 can be moved.

It should be noted that various other characteristics, aspects, features, etc. of a needle bending assembly may be selected to adjust a bend angle, such as the bend angle θ as indicated in FIGS. 29 and 30. While the shoulders 612 and 632 are described above as being translated or moved in a substantially linear direction along the first and second housing sections 611 and 631, respectively, in other embodiments, one or more shoulders of a needle bending assembly can be moved, adjusted, and/or reconfigured in any suitable manner. For example, one or more shoulders of a needle bending assembly (e.g., shoulders may be similar to the shoulders 612 and 632 as shown in FIGS. 29 and 30) may be configured to rotate about an axis (e.g., a bending axis defined by the coupling element), thereby changing a separation distance between the shoulders or contact surfaces thereof. Further, a shoulder may form a contact surface or the like having a shape which varies in a transverse direction (e.g., into or out of page or otherwise along the bending axis defined by the coupling element) such that a separation distance between the shoulders varies in the transverse direction. In such embodiments, one or more of the shoulders may be configured to move in the transverse direction, thereby adjusting the separation distance between the shoulders based at least in part on the position of the shoulder(s) in the transverse direction. In other embodiments, one or both of the shoulders may have sections that can be removed (e.g., broken away), thereby modifying a shape and/or size of the one or both of the shoulders and, in turn, a separation distance between the shoulders. Accordingly, one or more of the above movements or modifications of the shoulders (or any other suitable movement or modification) may allow for further control and/or adjustment of the bend angle θ.

It should be appreciated that various other embodiments of a needle bending system may be used that include various ways to adjust parameters, distances, and the like of the components of the needle bending system. For instance, in one embodiment, a first housing section may be configured to move closer (or away) from a second housing section, thereby adjusting a length of a section of a needle located between the first housing section and the second housing section. Such adjustment may influence (e.g., increase or decrease) a curvature of the needle in a bend section of the needle (e.g., if the distance L between the first housing section and the second housing section is increased, the degree of curvature of the needle may decrease for the same amount or angle of rotation of the second housing section relative to the first needle section.

FIGS. 31-35 are various views of an example embodiment of a needle bending system 700 according to an embodiment. The needle bending system 700 includes a needle bending assembly 702 and a needle assembly 740 that is removably coupled to the needle bending assembly 702. The needle bending assembly 702 can include a first housing section 711, a second housing section 731, and a coupling element 721 that movably couples the housing sections. The needle bending system 700 can be similar in at least form and/or function to the needle bending system 200 described above with reference to FIGS. 2-18 and thus, portions and/or aspects of the needle bending system 700 and/or needle bending assembly 702 are not described in further detail herein. The embodiment shown in FIGS. 31-35, however, can differ from the needle bending system 200 in an arrangement and/or manner of engagement between the needle assembly 740 and the needle bending assembly 702. For example, in the embodiment shown in FIGS. 31-35, at least a portion of the needle bending assembly 702 has been configured and/or otherwise has been adapted to selectively engage and/or receive a portion of the needle assembly 740 to, for example, facilitate alignment and/or positioning of a known needle assembly relative to the needle bending assembly 702.

Figure 31:
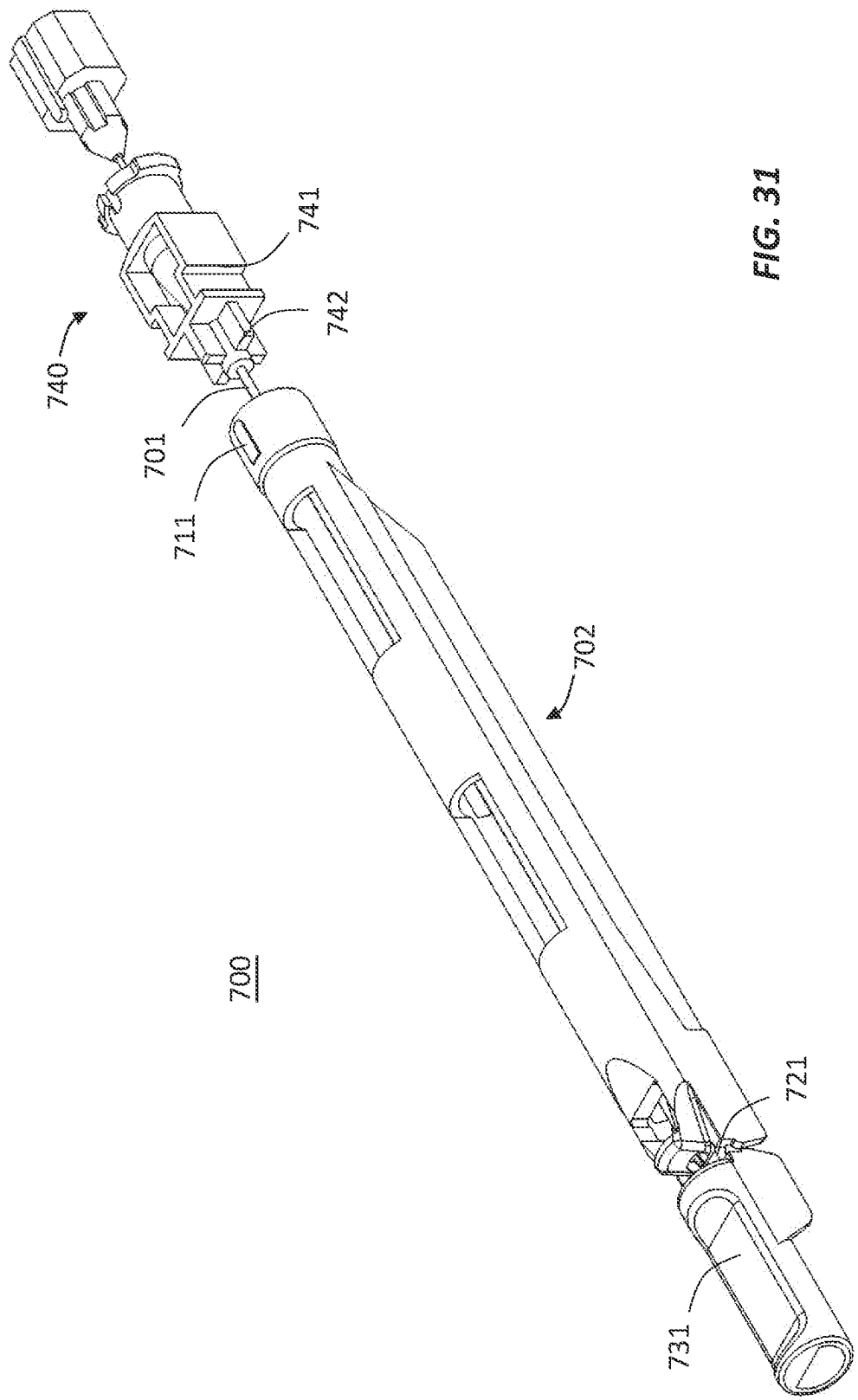
FIGS. 31 and 32 are a front perspective view and a rear perspective view, respectively, of a needle bending system showing a needle assembly removably coupled to a needle bending assembly, according to an embodiment.
Figure 32:
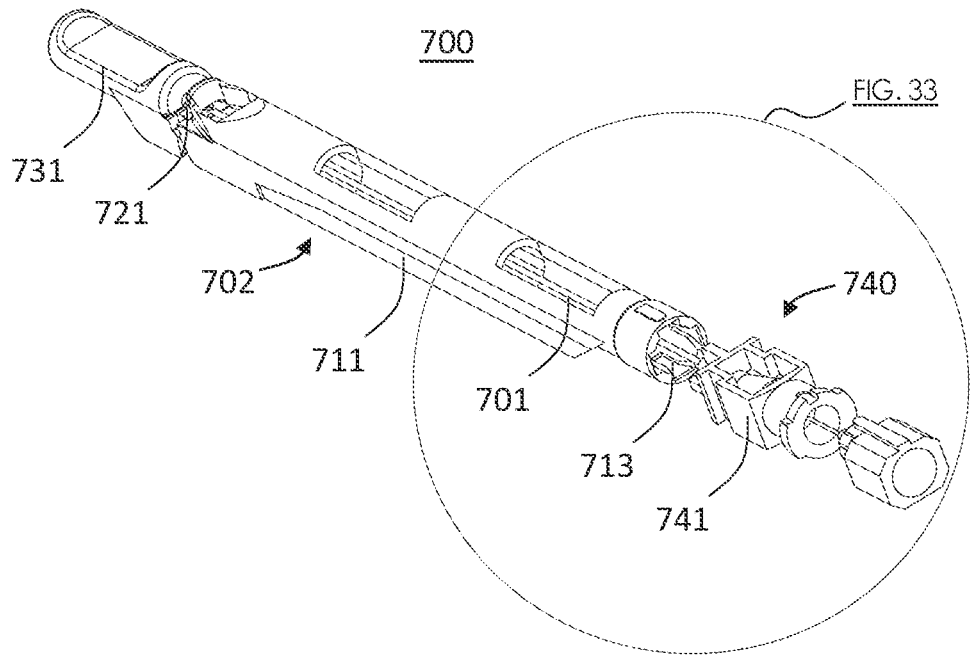
Figure 33:
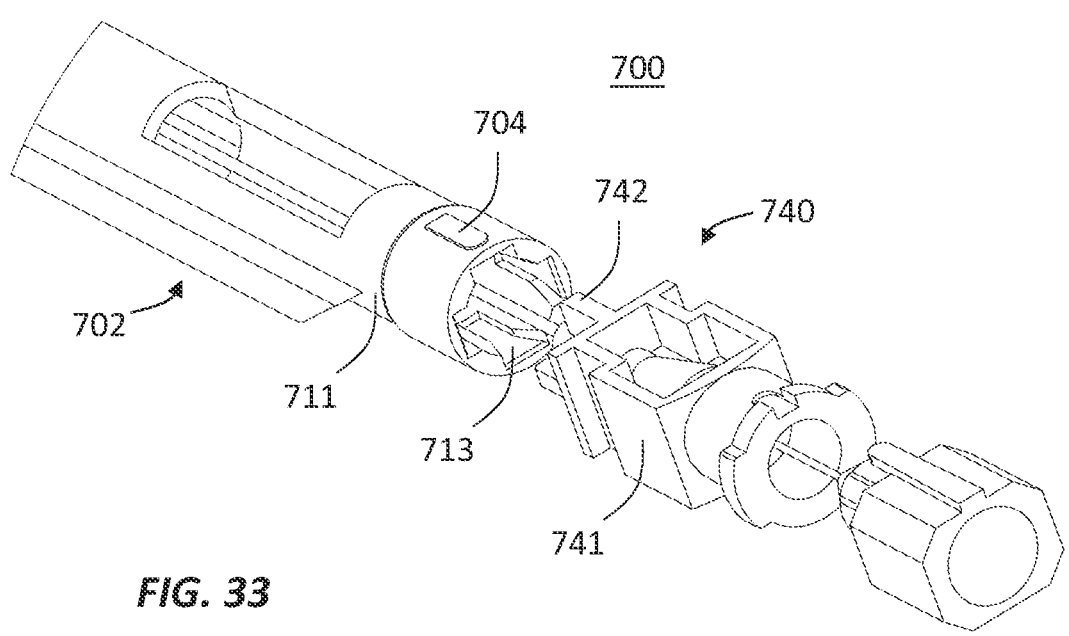
FIG. 33 is an enlarged view of a portion of the needle bending system identified by the circled region in FIG. 32.

For example, in some implementations, the needle bending assembly 702 can be used with a known needle assembly such as a spinal needle made by Spectra Medical Devices, LLC (referred to herein as a Spectra Needle). For example, FIGS. 31-33 show the needle assembly 740 (e.g., a Spectra Needle) includes a needle hub 741 and a needle 701 coupled to and extending distally from the needle hub 741. In some implementations, the needle 701 and a distal end portion 742 of the needle hub 741 can be selectively received and/or inserted into a portion of the needle bending assembly 702 when the needle assembly 740 is removable coupled to the needle bending assembly 702. For example, the first housing section 711 has an inner surface that defines a cavity 713 configured to receive a portion of the needle 701 and the distal end portion 742 of the needle hub 741, as described in detail above with reference to the first cavity 213.

While some needle hubs may include a generally circular distal end portion, FIG. 31 shows the distal end portion 742 of the needle hub 741 including a set of protrusions that form a cross-shaped pattern. As shown in FIGS. 32 and 33, the inner surface at or along a proximal end portion of the first housing section 711 is shaped and/or sized to correspond to (or has a shape and/or size that is at least partially based on) the size, shape, and/or configuration of the distal end portion 742 of the needle 742. In this embodiment, for example, the inner surface defining the cavity 713 at or along the proximal end portion of the first housing section 711 can have and/or form a set of recesses, grooves, channels, and/or the like (referred to herein as "grooves 715") arranged in a cross-shaped pattern that substantially corresponds to the cross-shaped pattern of the distal end portion 742 of the needle hub 741.

Figure 34:
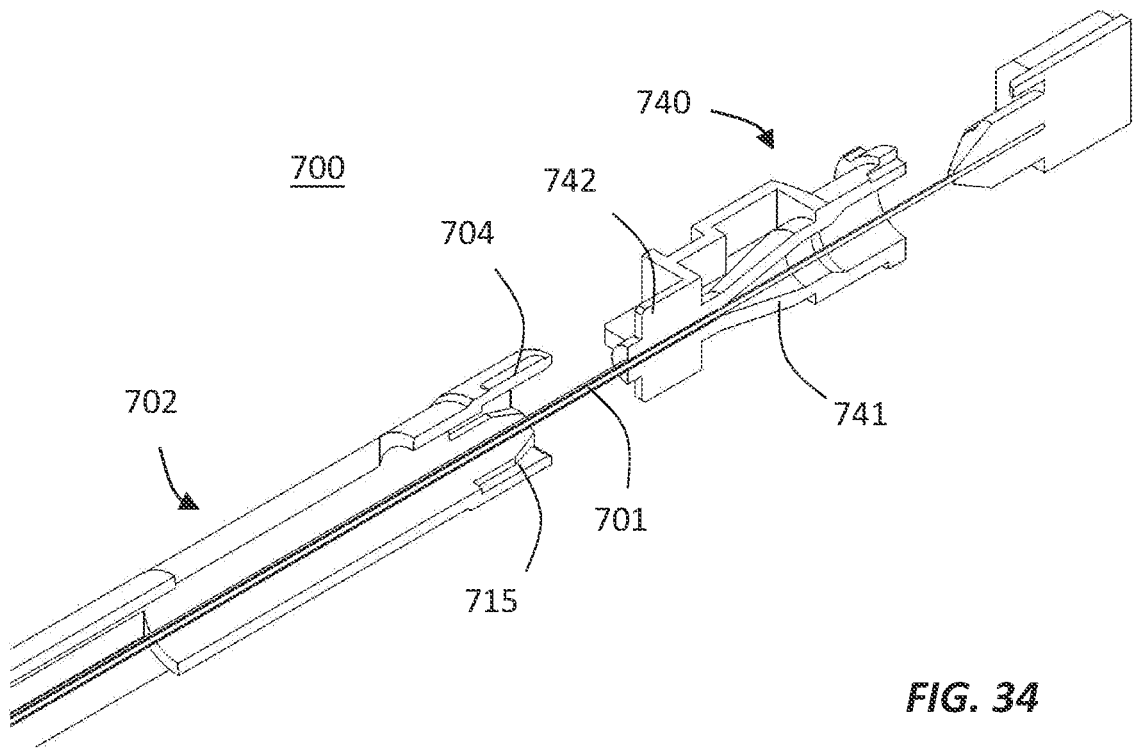
FIG. 34 is an enlarged cross-sectional view of a portion of the needle bending system of FIG. 31 showing the needle hub disengaged from a proximal end portion of the needle bending assembly.
Figure 35:
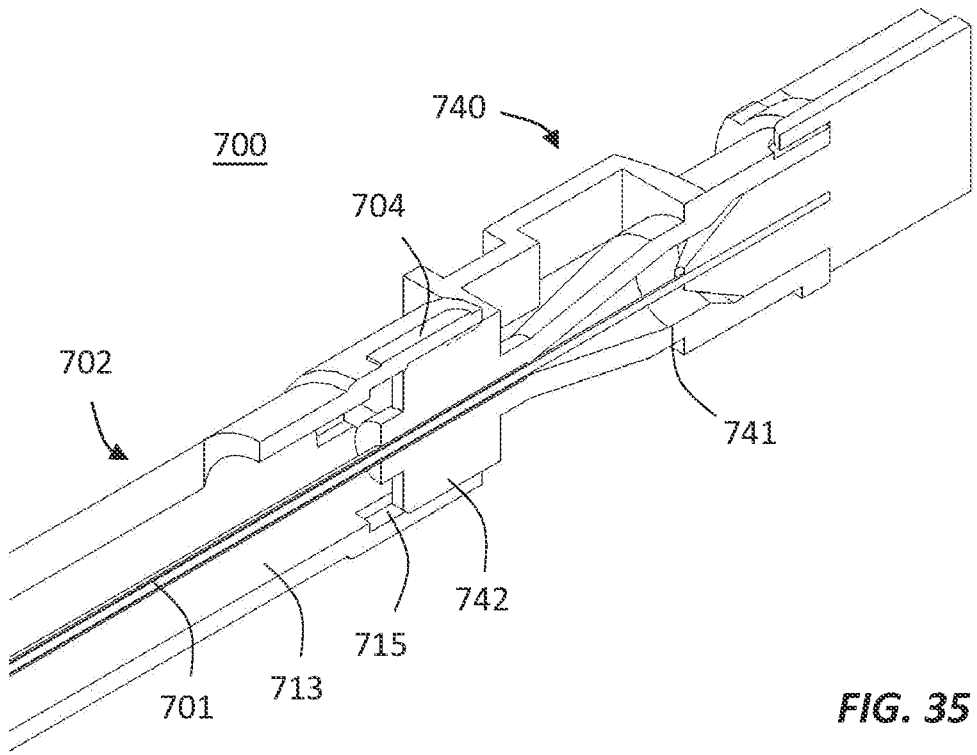
FIG. 35 is an enlarged cross-sectional view of a portion of the needle bending system of FIG. 31 showing the needle hub engaged with the proximal end portion of the needle bending assembly.

In some embodiments, the grooves 715 or at least a portion thereof can be oversized relative to the size of the protrusions of the needle hub 741 allowing for acceptable tolerances during manufacturing, assembly, and/or use. For example, the size, shape, and/or arrangement of the grooves 715 (or at least a portion of the grooves 715) can selectively allow the needle assembly 740 to be rotated or spun about a longitudinal axis thereof. As shown in FIG. 34, the grooves 715 or at least a portion thereof can be tapered or otherwise arranged in a funnel-like configuration. In some implementations, such an arrangement can provide and/or act as a self-centering feature that allows for a degree of misalignment as the distal end portion 742 of the needle hub 741 is inserted into the cavity 713 and that gradually directs or guides the needle hub 741 into alignment as it is advanced in a distal direction, as shown in FIG. 35. In addition, after bending the needle 701, the tapered or funnel-like arrangement of the grooves 715 can allow the needle assembly 740 to be rotated and/or spun to facilitate withdrawal of the needle 701 from the needle bending assembly 702 (e.g., in a manner similar to the needle bending system 300 shown in FIGS. 19-24).

FIGS. 33-35 also show the proximal end portion of the first housing section 711 including one or more indicators, keying features, alignment features, and/or the like (referred to as "alignment feature 704") that can be used to align or to verify an alignment of the needle assembly 740 relative to the needle bending assembly 702. The desired positioning and/or alignment of the needle assembly 740 relative to the needle bending assembly 702 can ensure or substantially ensure the needle 701 is bent in or along a desired portion or section of the needle 701. Similarly, the desired positioning and/or alignment of the needle assembly 740 relative to the needle bending assembly 702 can ensure or substantially ensure the needle 701 is bent in a desired direction (e.g., relatively to a beveled distal tip of the needle 701).

In some embodiments, the alignment feature 704 can selectively engage one or more surfaces of at the distal end portion 742 of the needle hub 741 to at least temporarily secure, restrain, and/or lock the needle hub 741 relative to the needle bending assembly 702. After bending, engaging and/or manipulating the alignment feature 704 can release and/or otherwise disengage the alignment feature 704 from the distal end portion 742 of the needle hub 741, thereby allowing the needle assembly 740 to be moved (e.g., withdrawn) relative to the needle bending assembly 702.

Any of the embodiments described herein can be used by a medical professional for bending a needle (e.g., a spinal needle) in a selected, predetermined, and/or desired way prior to, for example, inserting the needle into a patient. The needle bending systems described herein can allow for and/or provide a consistent, predictable, and/or repeatable needle bending (e.g., bending a needle by a prescribed, predetermined, and/or desired angle). In various embodiments, a needle bending system may be prepackaged and consist of a needle housed at least partially within a needle bending assembly. Further, the needle may be connected to a needle hub at a proximal end (outside of the needle bending assembly), while the distal end of the needle is or has been placed within the needle bending assembly. The medical professional may use the needle bending assembly to bend the needle at or near a distal end portion of the needle, and then retrieve or withdraw the needle from the needle bending assembly (e.g., by pulling on the needle hub).

Figure 36:
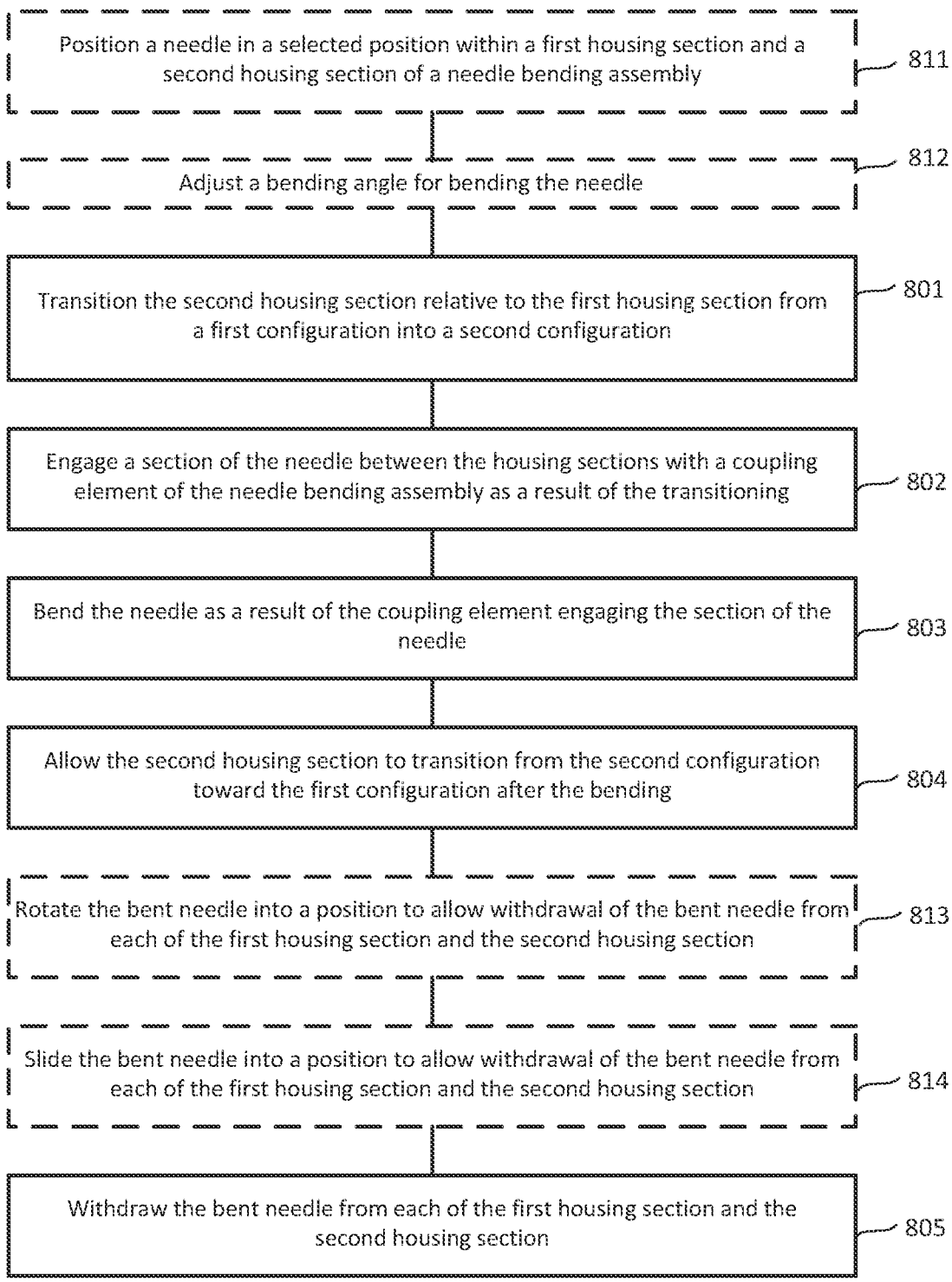
FIG. 36 is flowchart illustrating a method of bending a needle using a needle bending system, according to an embodiment.

FIG. 36 is a flowchart illustrating a method 800 of bending a needle using a needle bending system such as any of those described herein. In some implementations, for example, the needle can be predisposed in a needle bending assembly and/or system (referred to herein as needle bending assembly) having a first housing section, a second housing section, and a coupling element that couples the first and the second housing sections. The predisposing in the needle bending assembly can be, for example, during one or more manufacturing processes or steps (e.g., allowing the needle bending assembly and the needle to be sterilized and packaged together). Alternatively, a medical professional can dispose the needle in the needle bending assembly at the time of use (e.g., during a medical procedure). In this manner, the needle can be disposed in a selected position within the first housing section and the second housing section of the needle bending assembly.

With the needle positioned in the needle bending assembly, the method 800 of bending the needle includes transitioning the second housing section relative to the first housing section from a first configuration to a second configuration, at step 801. In an example embodiment, the transitioning includes rotating of the second housing section relative to the first housing section through a predetermined range of motion as described in detail above with respect to specific embodiments. For example, the needle bending assembly can be transitioned from a first (initial) configuration when the first housing section (or at least a portion or central axis thereof) is aligned with the second housing section (or at least a portion or central axis thereof) into a second configuration in which the second housing portion (or at least a portion or central axis thereof) is misaligned, moved, rotated, etc. relative to the first housing section (or at least a portion or central axis thereof) by a desired amount or angle, as described in detail above.

A section of the needle between the first housing section and the second housing section is engaged by a coupling element of the needle bending assembly as a result of the transitioning, at 802. For example, the needle can be positioned in the needle bending assembly (e.g., during manufacturing or prior to/during a medical procedure) such that the needle is placed in a desired position (e.g., axial position) relative to the coupling element. In this manner, the needle can be bent at or along a predetermined and/or desired section or length of the needle. In some implementations, for example, the predetermined and/or desired section or length of the needle can be based at least in part on the size and/or type of the needle, the medical procedure being performed or planned, the anatomy of the patient or anticipated anatomy of the patient, and/or the like.

The needle is bent as a result of the coupling element engaging the second of the needle, at 803. In some implementations, the transitioning of the second housing section and/or the positioning of the needle relative to the coupling element can allow the needle to be bent in a predetermined and/or desired way or amount. For example, in some embodiments, the first housing section and/or the second housing section can include one or more shoulders that can selectively control and/or limit relative movement between the first housing section and the second housing section, thereby controlling and/or limiting an amount or degree of bending along the section of the needle. Options and/or implementations for controlling an amount, degree, and/or position of the bend along the needle are described above with reference to specific embodiments. It should be understood, however, that these options and/or implementations are presented by way of example only and not limitation. Other feature(s), device(s), and/or method(s), or combinations thereof, for controlling and/or limiting the bend along the needle may be possible.

After bending the needle, the second housing section is allowed to transition (e.g., move, rotate, and/or the like) relative to the first housing section from the second configuration toward the first configuration, at 804. Said another way, after bending the needle, the second housing section may be transitioned or allowed to transition back to a substantially unmoved or substantially non-rotated configuration in which the second housing section (or at least a portion or central axis thereof) is aligned or substantially aligned with the first housing section (or at least a portion or central axis thereof). As such, the needle bending assembly and/or the housing sections thereof can be in a configuration resembling or similar to the first configuration, but the needle disposed in the needle bending assembly is now bent. At step 805, the bent needle can be withdrawn from each of the first housing section and the second housing section of the needle bending assembly. For example, in some embodiments, a proximal end of the needle can be coupled to and/or can extend distally from a needle hub, the needle and needle hub collectively forming a needle assembly. In such embodiments, the needle can be withdrawn from the housing sections by pulling and/or otherwise moving the needle hub in a proximal direction relative to the needle bending assembly.

In some implementations, the method 800 can include one or more additional (optional) steps. For example, at an optional step 811, the method 800 can include positioning the needle (e.g., moving, advancing, retracting, rotating, adjusting, and/or the like) to the selected position within and/or relative to the first housing section and/or the second housing section. In some embodiments, the needle bending assembly can include a window or other feature configured to allow a user to determine and/or visualize a relative position of a tip of the needle (e.g., such as the needle bending system 600 shown in relation to FIG. 30). In some implementations, the selected position may be determined by a position of a distal tip of the needle, as observed through a window located along the second housing section such that the bending of the needle occurs at or along the specified and/or desired needle section and/or otherwise at or along a desired length of the needle.

Additionally or alternatively, at optional step 812, the method 800 can include adjusting a bending angle for bending the needle. For example, in some implementations, the needle bending assembly includes a mechanism or device for adjusting a bend angle of the needle such as the dials 619 and/or 639 included in the needle bending system 600 shown in FIGS. 29 and 30, and/or any other suitable mechanism or device. As such, the mechanism(s), device(s), dial(s), etc. can be transitioned, moved, advanced, retracted, translated, rotated, and/or otherwise manipulated to, for example, adjust one or more shoulders of the needle bending assembly, thereby at least partially controlling the bend angle of the needle (e.g., increasing or decreasing) when the second housing section is transitioned, moved, and/or rotated from the first configuration to the second configuration.

Further, if the needle bending assembly includes first and second cavities which are similar or substantially the same as the first and second cavities 313 and 333, as shown in FIGS. 22-24, the method 800 can include at an optional step 813, rotating the bent needle to a position that allows the bent needle to be withdrawn (e.g., pulled in a proximal direction relative to the needle bending assembly) from and/or through the first cavity and the second cavity. For example, the bent needle can be rotated about the longitudinal or X axis by about 90 degrees, as described above in relation to FIG. 23. Additionally or alternatively, if the needle bending assembly includes first and second cavities which are similar or the substantially same as the first and second cavities 413 and 433, as shown in FIGS. 25 and 26, the method 800 can include at an optional step 814, sliding the bent needle to a position that allows the bent needle to be withdrawn (e.g., pulled in the proximal direction relative to the needle bending assembly) from and/or through the first housing section and the second housing section (or cavities thereof). For example, the bent needle can be slid or moved transversely (e.g., along a Z axis) within the first and second cavities to position the bent needle such that it can be pulled from the first and second housing sections.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are presented by way of example only and that the actual parameters, dimensions, materials, and/or configurations may depend upon the specific application or applications in which they are used. Those skilled in the art will recognize or be able to ascertain many equivalents to the specific embodiments described herein. It is, therefore, to be understood that the foregoing embodiments are presented by way of example only and that embodiments may be practiced in ways other than as specifically described and/or claimed.

Although embodiments have been described as having particular features and/or combinations of components, other embodiments are possible having a combination of any features and/or components from any of embodiments described herein, except mutually exclusive combinations. The embodiments described herein can include various combinations and/or sub-combinations of the functions, components, and/or features of the different embodiments described.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Also, various concepts may be embodied as one or more methods, of which example(s) has/have been provided. The acts performed as part of the method may be ordered in any suitable way. Accordingly, embodiments may be constructed in which acts are performed in an order different than illustrated, which may include performing some acts simultaneously or in parallel processes, when possible, even though described and/or shown as sequential acts in certain embodiments.

What is claimed is:

1. A needle bending assembly configured to at least temporarily contain a needle, the needle bending assembly comprising:
    a first housing section defining a first cavity configured to at least temporarily contain a first section of the needle;
    a second housing section defining a second cavity configured to at least temporarily contain a second section of the needle forming a distal tip thereof; and
    a coupling element coupled between the first housing section and the second housing section such that when the needle is contained within the needle bending assembly, movement of the second housing section relative to the first housing section results in a bending of the needle at a location corresponding to the coupling element,
    wherein the first housing section, the second housing section, and the coupling element are monolithically constructed.

2. The needle bending assembly of claim 1, wherein the first housing section includes an inner surface defining at least a portion of the first cavity, the inner surface configured to contact the first section of the needle when the needle is contained in the needle bending assembly.

3. The needle bending assembly of claim 1, wherein the second housing section is configured for movement relative to the first housing section through a predetermined range of motion between a first configuration and a second configuration.

4. The needle bending assembly of claim 3, wherein the second housing section includes an inner surface defining at least a portion of the second cavity, and
    when the needle is contained in the needle bending assembly, the inner surface being spaced apart from the second section of the needle when the second housing section is in the first configuration, the inner surface being placed in contact with the second section of the needle when the second housing section is in the second configuration.

5. The needle bending assembly of claim 1, wherein the coupling element includes a living hinge that couples the first housing section to the second housing section, the living hinge configured to be in contact with a third section of the needle between the first section and the second section of the needle.

6. The needle bending assembly of claim 5, wherein the movement of the second housing section relative to the first housing section results in the bending of the needle at a location along the third section of the needle, a fulcrum about which the needle is bent corresponding to a point of contact between the living hinge and the third second of the needle.

7. The needle bending assembly of claim 1, wherein the first housing section includes an inner surface defining at least a portion of the first cavity, the second housing section includes an inner surface defining at least a portion of the second cavity, and when the needle is contained in the needle bending assembly:
    the inner surface of the first housing section is configured to contact the first section of the needle,
    the inner surface of the second housing section is spaced apart from the second section of the needle when the second housing section is in a first configuration relative to the first housing section, and
    the inner surface of the second housing section is placed in contact with the second section of the needle when the second housing section is moved to a second configuration relative to the first housing section, the contact operable to bend the needle at the location corresponding to the coupling element, and
    the inner surface of the first housing section and the inner surface of the second housing section being shaped to allow withdrawal of the needle from each of the first cavity and the second cavity after bending.

8. A needle bending system, comprising:
    a needle assembly having a needle extending in a distal direction from a needle hub; and
    a needle bending assembly removably coupled to the needle assembly, the needle bending assembly including:
        a first housing section defining a first cavity that removably contains a first section of the needle,
        a second housing section defining a second cavity that removably contains a second section of the needle forming a distal tip thereof, and
        a coupling element configured to couple the first housing section and the second housing section such that movement of the second housing section relative to the first housing section results in a bending of the needle at a location corresponding to the coupling element,
        wherein the first housing section, the second housing section, and the coupling element are monolithically constructed.

9. The needle bending system of claim 8, wherein the first housing section includes an inner surface defining at least a portion of the first cavity, the inner surface in selective contact with the first section of the needle.

10. The needle bending system of claim 8, wherein a distal portion of the needle hub is removably disposed in a proximal portion of the first cavity to removably couple the needle hub to the needle bending assembly,
    the inner surface defining the proximal portion of the first cavity forms a plurality of recesses, each recess from the plurality of recesses being aligned with and receiving a portion of a unique protrusion from a plurality of protrusions along the distal portion of the needle hub.

11. The needle bending system of claim 8, wherein the second housing section is configured for movement relative to the first housing section through a predetermined range of motion between a first configuration and a second configuration.

12. The needle bending system of claim 11, wherein the second housing section includes an inner surface defining at least a portion of the second cavity, the inner surface being spaced apart from the second section of the needle when the second housing section is in the first configuration, the inner surface being placed in contact with the second section of the needle when the second housing section is in the second configuration.

13. The needle bending system of claim 8, wherein the coupling element includes a living hinge that couples the first housing section to the second housing section, the movement of the second housing section relative to the first housing section bends the needle at a location along the third section of the needle, a fulcrum about which the needle is bent corresponding to a point of contact between the living hinge and a third section of the needle between the first section and the second section of the needle.

14. The needle bending system of claim 8, wherein the first housing section includes an inner surface defining at least a portion of the first cavity and the second housing section includes an inner surface defining at least a portion of the second cavity,
   the inner surface of the first housing section is in selective contact with the first section of the needle,
   the inner surface of the second housing section is spaced apart from the second section of the needle when the second housing section is in a first configuration relative to the first housing section, the inner surface of the second housing section is placed in contact with the second section of the needle when the second housing section is moved to a second configuration relative to the first housing section, the contact operable to bend the needle at the location corresponding to the coupling element, and
   the inner surface of the first housing section and the inner surface of the second housing section being shaped to allow withdrawal of the needle from each of the first cavity and the second cavity after bending.

15. A method of bending a needle using a needle bending assembly, the needle bending assembly including a first housing section, a second housing section, and a coupling element that couples the first housing section to the second housing section, wherein the first housing section, the second housing section, and the coupling element being monolithically constructed, the method comprising:
   transitioning the second housing section relative to the first housing section from a first configuration into a second configuration;
   engaging a section of the needle between the housing sections with the coupling element as a result of the transitioning;
   bending the needle as a result of the coupling element engaging the section of the needle;
   allowing the second housing section to transition from the second configuration toward the first configuration after the bending; and
   withdrawing the bent needle from each of the first housing section and the second housing section.

16. The method of claim 15, wherein the transitioning includes bending the second housing section relative to the first housing section through a predetermined angle of rotation and about a fulcrum defined by the coupling element.

17. The method of claim 16, wherein the predetermined angle of rotation is greater than an angle of the bend along the needle.

18. The method of claim 15, wherein the coupling element is a living hinge that movably couples the first housing section and the second housing section.

19. The method of claim 15, wherein after allowing the second housing to transition toward the first configuration and prior to withdrawing the bent needle from each of the first housing section and the second housing section, the method further comprising:
   repositioning the bent needle in the needle bending assembly to allow withdrawal of the bent needle from each of the first housing section and the second housing section, the repositioning including at least one of rotating or sliding the bent needle relative to the needle bending assembly.

* * * * *